United States Patent
Mah

(10) Patent No.: US 10,007,988 B2
(45) Date of Patent: Jun. 26, 2018

(54) SYSTEMS AND METHODS FOR APPROXIMATING THE SOFT TISSUE PROFILE OF THE SKULL OF AN UNKNOWN SUBJECT

(71) Applicant: The Board of Regents of the Nevada System of Higher Education on Behalf of the University of Nevada, Las Vegas, Las Vegas, NV (US)

(72) Inventor: James Mah, Las Vegas, NV (US)

(73) Assignee: The Board of Regents of the Nevada System of Higher Education on Behalf of the University of Nevada, Las Vegas, Las Vegas, NV (US)

( * ) Notice: Subject to any disclaimer, the term of this patent is extended or adjusted under 35 U.S.C. 154(b) by 0 days. days.

(21) Appl. No.: 15/121,895

(22) PCT Filed: Feb. 27, 2015

(86) PCT No.: PCT/US2015/018086
§ 371 (c)(1),
(2) Date: Aug. 26, 2016

(87) PCT Pub. No.: WO2015/131091
PCT Pub. Date: Sep. 3, 2015

(65) Prior Publication Data
US 2017/0018084 A1 Jan. 19, 2017

Related U.S. Application Data

(60) Provisional application No. 61/945,970, filed on Feb. 28, 2014.

(51) Int. Cl.
*G06K 9/00* (2006.01)
*G06T 7/00* (2017.01)
(Continued)

(52) U.S. Cl.
CPC .......... *G06T 7/0016* (2013.01); *A61B 5/0077* (2013.01); *A61B 5/055* (2013.01);
(Continued)

(58) Field of Classification Search
CPC .......... G06K 9/00221; G06K 9/00208; G06K 9/00295; A61B 6/032; A61B 5/055;
(Continued)

(56) References Cited

U.S. PATENT DOCUMENTS

| 5,813,984 A | 9/1998 | Haaga et al. |
| 2006/0111631 A1 | 5/2006 | Kelliher et al. |

(Continued)

FOREIGN PATENT DOCUMENTS

WO WO-2015/131091 A1 9/2015

OTHER PUBLICATIONS

Cangialosi TJ, et al., "The ABO discrepancy index: a measure of case complexity," Am J Orthod Dentofacial Orthop. (2004) 125(3):270-8.
(Continued)

*Primary Examiner* — Yon Couso
(74) *Attorney, Agent, or Firm* — Ballard Spahr LLP

(57) ABSTRACT

Facial approximation systems and methods for approximating the soft tissue profile of the skull of an unknown subject.

22 Claims, 19 Drawing Sheets

(51) Int. Cl.
  *A61B 5/00* (2006.01)
  *A61B 5/055* (2006.01)
  *A61B 6/03* (2006.01)
  *A61B 6/00* (2006.01)
  *A61B 8/08* (2006.01)

(52) U.S. Cl.
  CPC ............ *A61B 6/032* (2013.01); *A61B 6/4085* (2013.01); *A61B 6/501* (2013.01); *A61B 8/0875* (2013.01); *G06K 9/00208* (2013.01); *G06K 9/00221* (2013.01); *G06K 9/00295* (2013.01); *G06T 2200/24* (2013.01); *G06T 2207/10081* (2013.01); *G06T 2207/10088* (2013.01); *G06T 2207/10132* (2013.01); *G06T 2207/30008* (2013.01); *G06T 2207/30024* (2013.01)

(58) Field of Classification Search
  CPC ..... A61B 5/0077; A61B 8/0875; A61B 6/501; A61B 6/4085; G06T 7/0016; G06T 2207/30008; G06T 2207/10132; G06T 2207/10088; G06T 2207/10081; G06T 2200/24; G06T 2207/30024; G06T 7/00; G06T 7/0012; G06T 7/0014; G06T 7/0022; G06T 7/0024; G06T 7/0026; G06T 7/0028
  See application file for complete search history.

(56) References Cited

U.S. PATENT DOCUMENTS

| | | |
|---|---|---|
| 2009/0003667 A1 | 1/2009 | Cheng et al. |
| 2012/0182294 A1 | 7/2012 | Cordon Garcia et al. |
| 2013/0217996 A1 | 8/2013 | Finkelstein et al. |
| 2014/0348405 A1* | 11/2014 | Chen .................. G06T 7/60 382/131 |
| 2016/0203604 A1* | 7/2016 | Gupta .................. G06K 9/52 382/128 |
| 2017/0258420 A1* | 9/2017 | Inglese .................. A61B 6/14 |

OTHER PUBLICATIONS

El-Fegh I, et al., "Automated 2-D cephalometric analysis of X-ray by image registration approach based on least square approximator," CofProc IEEE Eng Med Bioi Soc. (2008) 2008:3949-52.

Hsiao, T -H, et al., "Sex determination using discriminant function analysis in children and adolescents: a lateral cephalometric study," Int J Legal Med (2010) 124:155-160.

Leonardi R, et al., "An evaluation of cellular neural networks for the automatic identification of cephalometric landmarks on digital images," J Biomed Biotechnol. (2009) 2009:717102.

Nejat, et al., "A Forensic Identification Utility to Create Facial Approximations using Cone-Beam Computed Tomography of 100 Hispanic Females: A Pilot Study," UNLV Theses/Dissertations/Professional Papers/Capstones (Dec. 1, 2012) (108 pages).

Rueda S, et al., "An approach for the automatic cephalometric landmark detection using mathematical morphology and active appearance models," Med Image Comput Comput Assist Interv. (2006) 9(Pt 1): 159-66.

Sommer T, et al., "Precision of cephalometric analysis via fully and semiautomatic evaluation of digital lateral cephalographs," Dentomaxillofac Radiol. (2009) 38(6):401-6.

Stamm T, et al., "Computer-aided automated landmarking of cephalograms," J Orofac Orthop. (1998) 59(2):73-81.

International Search Report and Written Opinion was dated Jun. 11, 2015 by the International Searching Authority for PCT Application PCT/US2015/018086, which was filed on Feb. 27, 2015 and published as WO/2015/131091 on Sep. 3, 2015 (Applicant—University of Nevada; Inventor—James Mah) (8 Pages).

\* cited by examiner

| Measure | Rank | Weight | Scaled Weight |
|---|---|---|---|
| Björk-Jarabak Analysis | | | |
| N-S-Ar | 1.0 | 1.0000 | 0.0750 |
| S-Ar-Go | 2.0 | 0.5000 | 0.0375 |
| Ar-Go-N | 2.0 | 0.5000 | 0.0375 |
| N-Go-Me | 2.0 | 0.5000 | 0.0375 |
| N-S / S-Ar | 1.0 | 1.0000 | 0.0750 |
| N-Me / S-Go | 1.5 | 0.6667 | 0.0500 |
| N-ANS / ANS-Me | 1.0 | 1.0000 | 0.0750 |
| Steiner Analysis | | | |
| S-N-A | 1.0 | 1.0000 | 0.0750 |
| S-N-B | 1.0 | 1.0000 | 0.0750 |
| A-N-B | 1.0 | 1.0000 | 0.0750 |
| S-N-Go-Gn | 1.5 | 0.6667 | 0.0500 |
| U1-SN | 2.0 | 0.5000 | 0.0375 |
| IMPA | 2.0 | 0.5000 | 0.0375 |
| Downs Analysis | | | |
| FMA | 1.5 | 0.6667 | 0.0500 |
| Nasal Approximation | | | |
| S-N-Rhi | 1.0 | 1.0000 | 0.0750 |
| Rhi-S-A | 3.0 | 0.3333 | 0.0250 |
| N-S-ANS | 2.0 | 0.5000 | 0.0375 |
| N-S-A | 2.0 | 0.5000 | 0.0375 |
| N-ANS-Rhi | 2.0 | 0.5000 | 0.0375 |

FIG. 6

|                 | Face 1 | Face 2 | Face 3 | Face 4 | Face 5 | Face 6 |
|-----------------|--------|--------|--------|--------|--------|--------|
| Face Pool One | | | | | | |
| Algorithm rank  | ∞      | 3      | 1      | 2      | ∞      | ∞      |
| Algorithm score | 534    | 199    | 179    | 189    | 119    | 56     |
| Face Pool Two | | | | | | |
| Algorithm rank  | ∞      | 3      | 1      | 2      | ∞      | ∞      |
| Algorithm score | 534    | 199    | 179    | 189    | 119    | 56     |
| Face Pool Three | | | | | | |
| Algorithm rank  | ∞      | 3      | 1      | 2      | ∞      | ∞      |
| Algorithm score | 534    | 199    | 179    | 189    | 119    | 56     |

FIG. 7

| | Face Pool One | | | | | |
|---|---|---|---|---|---|---|
| | Face 1 | Face 2 | Face 3 | Face 4 | Face 5 | Face 6 |
| | 4 | 2 | 1 | 5 | 3 | 6 |
| | 5 | 3 | 1 | 2 | 4 | 6 |
| | 6 | 5 | 3 | 2 | 4 | 1 |
| | 5 | 3 | 2 | 1 | 4 | 6 |
| | 2 | 4 | 3 | 1 | 5 | 6 |
| | 5 | 4 | 1 | 3 | 2 | 4 |
| | 6 | 4 | 4 | 1 | 5 | 2 |
| | 6 | 5 | 2 | 1 | 3 | 2 |
| | 6 | 4 | 3 | 1 | 5 | 3 |
| | 5 | 4 | 2 | 3 | 6 | 2 |
| | 6 | 5 | 1 | 2 | 4 | 1 |
| | 5 | 4 | 2 | 5 | 6 | 3 |
| | 3 | 1 | 6 | 1 | 6 | 4 |
| | 2 | 5 | 6 | 1 | 4 | 3 |
| Median assessed rank: | 5.0 | 4.0 | 2.0 | 2.0 | 4.5 | 3.0 |
| Mode assessed rank: | 5 | 4 | 1 | 1 | 4 | 6 |
| Algorithm rank: | 6 | 3 | 1 | 2 | 5 | 6 |
| Algorithm score: | 5.34 | 1.99 | 1.79 | 1.89 | 3.19 | 5.6 |

FIG. 9

| Face Pool Two | | | | | | |
|---|---|---|---|---|---|---|
| | Face 1 | Face 2 | Face 3 | Face 4 | Face 5 | Face 6 |
| Expert Assessed Ranks (n=14) | 1 | 2 | 6 | 5 | 3 | 4 |
| | 2 | 5 | 6 | 3 | 1 | 4 |
| | 3 | 6 | 5 | 3 | 2 | 4 |
| | 2 | 5 | 6 | 2 | 1 | 4 |
| | 1 | 4 | 5 | 3 | 1 | 6 |
| | 1 | 6 | 5 | 3 | 2 | 4 |
| | 2 | 3 | 6 | 2 | 5 | 4 |
| | 1 | 4 | 6 | 3 | 1 | 5 |
| | 2 | 5 | 4 | 2 | 3 | 4 |
| | 1 | 6 | 6 | 3 | 1 | 5 |
| | 2 | 5 | 5 | 4 | 3 | 4 |
| | 1 | 6 | 4 | 3 | 1 | 3 |
| | 1 | 5 | 6 | 3 | 2 | 5 |
| | 1 | 5 | 6 | 3 | 2 | 4 |
| Median assessed rank: | 1.0 | 5.0 | 6.0 | 3.0 | 2.0 | 4.0 |
| Mode assessed rank: | 1 | 5 | 6 | 3 | 1 | 4 |
| Algorithm rank: | 3 | 4 | 2 | 6 | 1 | 5 |
| Algorithm score: | 2.97 | 3.5 | 2.75 | 4.21 | 2.65 | 3.54 |

| | Face Pool Three ||||||
|---|---|---|---|---|---|---|
| | Face 1 | Face 2 | Face 3 | Face 4 | Face 5 | Face 6 |
| Expert Assessed Ranks (n = 14) | 2 | 1 | 3 | 4 | 5 | 6 |
| | 2 | 1 | 3 | 5 | 4 | 6 |
| | 4 | 5 | 3 | 2 | 6 | 1 |
| | 1 | 2 | 4 | 6 | 3 | 5 |
| | 1 | 2 | 6 | 3 | 5 | 4 |
| | 2 | 1 | 3 | 5 | 4 | 6 |
| | 2 | 1 | 5 | 6 | 3 | 4 |
| | 4 | 1 | 2 | 6 | 5 | 3 |
| | 2 | 1 | 4 | 6 | 3 | 5 |
| | 2 | 1 | 3 | 6 | 5 | 4 |
| | 2 | 1 | 5 | 6 | 4 | 3 |
| | 2 | 1 | 6 | 5 | 3 | 4 |
| | 1 | 2 | 4 | 6 | 3 | 5 |
| | 2 | 1 | 3 | 5 | 4 | 6 |
| *Median assessed rank:* | 2.0 | 1.0 | 3.5 | 5.5 | 4.0 | 4.5 |
| *Mode assessed rank:* | 2 | 1 | 3 | 6 | 3 | 6 |
| *Algorithm rank:* | 1 | 3 | % | % | 2 | % |
| *Algorithm score:* | 2.77 | 3.15 | 8.69 | 5.74 | 2.87 | 7.13 |

32, 34

```
┌─────────────────────────────────────────────────────────┐
│ Measure a plurality of selected cephalometric characteristics │
│   of a skull of an unknown subject to produce an unknown │
│                    skeletal dataset.                    │
└─────────────────────────────────────────────────────────┘
                              ▼
┌─────────────────────────────────────────────────────────┐
│   Access a database comprising a plurality of known skeletal │
│                         datasets.                       │
└─────────────────────────────────────────────────────────┘
                              ▼
┌─────────────────────────────────────────────────────────┐
│  Compare, through a processor in operative communication │
│   with the database, the unknown skeletal dataset to the │
│          plurality of known skeletal datasets.          │
└─────────────────────────────────────────────────────────┘
                              ▼
┌─────────────────────────────────────────────────────────┐
│    Determine, through the processor, the known skeletal │
│    dataset that most closely matches the unknown skeletal │
│                         dataset.                        │
└─────────────────────────────────────────────────────────┘
                              ▼
┌─────────────────────────────────────────────────────────┐
│   Display an image corresponding to the known skeletal  │
│   dataset that most closely matches the unknown skeletal │
│                         dataset.                        │
└─────────────────────────────────────────────────────────┘
```

FIG. 14

| Results for Pre-Treatment | | | | | | |
|---|---|---|---|---|---|---|
| Measurement | Dev. | Patient | Average | S.D. | Low | High |
| Facial Angle #1048 | * | 85.9 deg | 89.0 deg | 2.7 deg | 86.3 deg | 91.7 deg |
| Angle of convexity #77 | | 3.7 deg | 0.0 deg | 5.0 deg | -5.0 deg | 5.0 deg |
| S-N-A #9 | * | 78.2 deg | 82.0 deg | 2.0 deg | 80.0 deg | 84.0 deg |
| S-N-B #18 | ** | 75.8 deg | 80.0 deg | 2.0 deg | 78.0 deg | 82.0 deg |
| A-N-B #19 | | 2.4 deg | 2.0 deg | 1.5 deg | 2.0 deg | 3.5 deg |
| Palatal Plane to SN #1049 | ** | 6.8 deg | 8.0 deg | 0.5 deg | 7.5 deg | 8.5 deg |
| Anatomic Occl. Plane to SN #1 | *** | 24.4 deg | 14.5 deg | 1.0 deg | 13.5 deg | 15.5 deg |
| SN GoGn #21 | | 35.3 deg | 32.0 deg | 4.0 deg | 28.0 deg | 36.0 deg |
| Y-axis to FH #79 | | 59.2 deg | 0.0 deg | 0.0 deg | 0.0 deg | 0.0 deg |
| Y-as to SN #78 | | 68.8 deg | 67.0 deg | 4.0 deg | 63.0 deg | 71.0 deg |
| Percent LFH #1051 | | 58.7 % | 55.0 % | 0.0 % | 0.0 % | 0.0 % |
| ANS-Me #1026 | | 72.3 mm | 0.0 mm | 0.0 mm | 0.0 mm | 0.0 mm |
| N-ME #1052 | | 123.1 mm | 0.0 mm | 0.0 mm | 0.0 mm | 0.0 mm |
| U1 to SN #52 | ** | 99.9 deg | 104.0 deg | 2.0 deg | 100.0 deg | 104.0 deg |
| +1 to NA #23 | | 21.7 deg | 22.0 deg | 2.0 deg | 20.0 deg | 24.0 deg |
| +1 to NA #22 | | 5.6 mm | 4.0 mm | 2.0 mm | 2.0 mm | 6.0 mm |
| -1 to NB #25 | | 24.1 deg | 25.0 deg | 3.0 deg | 22.0 deg | 28.0 deg |
| -1 to NB #24 | | 5.7 mm | 4.0 mm | 2.0 mm | 2.0 mm | 6.0 mm |
| Pg to NB #26 | * | 1.2 mm | 4.0 mm | 2.0 mm | 2.0 mm | 6.0 mm |
| UI-LI (inter-incisal ang.) #8 | | 131.8 deg | 130.0 deg | 4.0 deg | 129.0 deg | 142.0 deg |
| -1 to APo #166 | | 3.6 mm | 2.0 mm | 2.0 mm | 0.3 mm | 5.0 mm |
| Upper Lip to E-Line #1044 | * | -0.7 mm | -4.0 mm | 2.0 mm | -6.0 mm | -2.0 mm |
| Lower Lip to E-Line #1-045 | *** | 4.4 mm | -4.0 mm | 2.0 mm | -6.0 mm | -2.0 mm |
| FMA #106 | * | 28.8 deg | 26.0 deg | 2.0 deg | 20.0 deg | 30.0 deg |
| -1 to mand plane #31 | ** | 90.0 deg | 95.0 deg | 2.0 deg | 88.0 deg | 92.0 deg |
| FMA #32 | * | 61.2 deg | 65.0 deg | 2.0 deg | 63.0 deg | 67.0 deg |

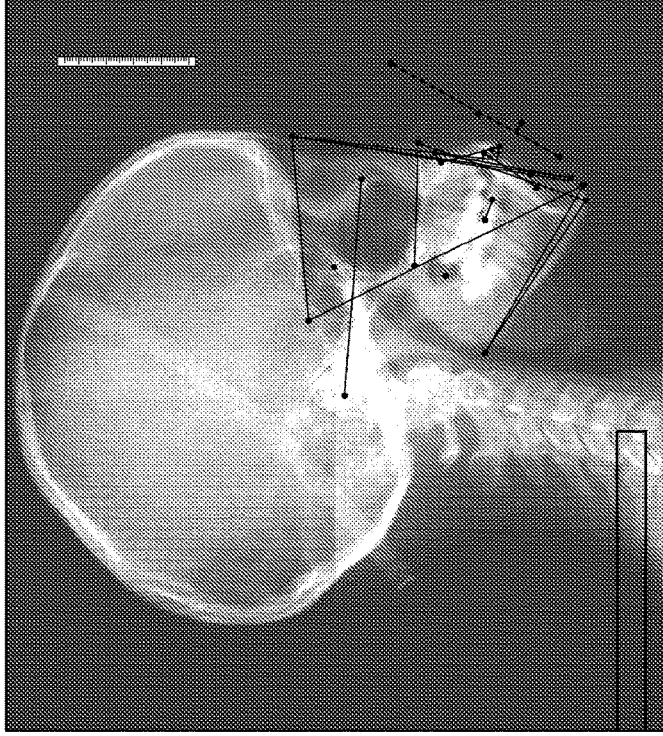

FIG. 16

SYSTEMS AND METHODS FOR APPROXIMATING THE SOFT TISSUE PROFILE OF THE SKULL OF AN UNKNOWN SUBJECT

CROSS-REFERENCE TO RELATED APPLICATION

This application claims the benefit of and priority under 35 U.S.C. § 371 to PCT/US2015/018086, filed Feb. 27, 2015, which claims the benefit under 35 U.S.C. § 119(e) to U.S. Provisional Patent Application No. 61/945,970, filed Feb. 28, 2014, which applications are incorporated herein by reference in their entireties.

BACKGROUND

In 2012, the U.S. Department of Justice reported that 797,500 children younger than 18 went missing. On average, 2,185 children are reported missing each day. Unfortunately, children, or adults, that go missing are often found dead. When skeletal remains are found, the medical and legal communities typically rely on the skeletal remains to provide important facts about the individual. Often, the skull is sufficiently preserved to be used in forensic investigations. Forensic experts can provide a basic sketch of an unknown individual based on the skull, but such basic sketches are often time-consuming and too inaccurate to permit identification of the individual.

The technique of forensic facial reconstruction can greatly expedite otherwise lengthy identification investigations and serve to stimulate the memory of the public in order to identify unknown individuals. The aim is to obtain an approximate representation of the real face to suggest a resemblance to a missing person. The usefulness of this technique has been well documented in the study of war crime victims and in mass disasters worldwide.

Craniofacial identification has undergone significant technical maturation, beginning with two-dimensional (2D) and three-dimensional (3D) manual methods and more recent 2D and 3D computer assisted methods. The process began in 19th century Europe—artisans modeled clay in bulk over soft tissue depth markers placed at various locations on the skull, without much regard for the underlying anatomy. More recently in the United States, this method has been modified and standardized in an American method, which consists of building soft tissue layers in bulk, without consideration of the underlying anatomy, approximating tabulated tissue depths in key locations and interpolating between these landmarks. During the same period, other researchers developed a Russian method of craniofacial reconstruction that modeled the musculature of the face, muscle by muscle, onto the skull. The strategy behind this technique is that the placement of the muscles and soft tissues covered by a thin layer will lead to a more accurate representation. However, this method requires estimation of the points of muscle attachment, muscle thickness, and the appearance of the soft tissue layer covering the muscle. Further advances include efforts to include estimations for mouth width, eyeball projection, ear height, nose projection, pronasale position, superciliare position, lip closure line, and lip position. Despite this progress, current craniofacial identification methods have major limitations. Firstly, all methods are largely based on soft tissue depth prediction models, a process that has never been empirically tested. Secondly, facial approximation practitioners recognize that, with few exceptions, the location and size of the facial muscles cannot be accurately established. This is a consequence of muscles which originate and/or insert into the soft tissue alone, and do not interface directly with the skull, making accurate prediction unlikely. Thirdly, assessment methods to test the accuracy of facial reconstruction techniques are isolated and not well established. Accuracy is a challenging metric to assess since reconstructions need not closely resemble a suspect to be identified as that specific person. These limitations result in a current system which is technically sensitive, subjective, and reliant on artistic interpretation. Furthermore, since these facial reconstructions are costly and time-consuming, they are generally limited to a single reconstruction or not done at all. Collectively, these limitations restrict the power of current forensic facial reconstruction methods in investigations, leaving many cases unresolved.

With the exception of computerization of some methods, few changes have been introduced into the process of approximating a human face. Comprehensive reviews of these approaches have shown that the computerized systems virtually mimic manual methods of clay reconstruction, using digital tissue depth markers and algorithms to produce a smooth face-mesh over these markers. Some recent systems involve volume deformation models, which consist of soft tissue warping, where the face of an anthropologically similar individual (age, sex, race) is warped onto the matched soft-tissue markers of the unknown skull. Statistical and vector-based models have recently been proposed to mathematically reconstruct the most likely soft tissue match for a skull. A recent conceptual framework and review of computerized craniofacial reconstruction (FIG. 1) summarizes the technical steps of building a digital craniofacial model, beginning with selection of an appropriate template and consideration of bias in its selection, incorporation of explicit knowledge relating to facial surfaces, craniofacial deformation to geometrically align with the target skull, and finally registration of the model to the skull by a fitting/matching process. A concern with this multi-step approach is the variability, error, and subjectivity that occur at each step. At this time, mainstream digital approaches are not employed by forensic investigators. The inefficiency and inaccuracies inherent in current methods of facial approximation warrant the exploration of other estimation-based methods.

Accordingly, there is a need in the art for a faster, more accurate, and more objective system and method for approximating the soft tissue profile of a skull of an unknown individual.

SUMMARY

Disclosed herein, in one aspect, is a facial approximation system for approximating a soft tissue profile of a skull of an unknown subject. The facial approximation system can comprise an imaging system configured to measure a plurality of selected cephalometric characteristics of the skull of the unknown subject. The facial approximation system can further comprise a database comprising a plurality of skeletal datasets, wherein each skeletal dataset is associated with a known subject and is indicative of a plurality of selected cephalometric characteristics of a skull of the known subject. The facial approximation system can further comprise a processor in operative communication with the database and the imaging system. The processor can be configured to compare the plurality of selected cephalometric characteristics of the skull of the unknown subject to the plurality of skeletal datasets. The processor can be further configured to determine the skeletal dataset of the plurality of skeletal datasets that most closely matches the soft tissue profile of the unknown subject.

In another aspect, disclosed herein is a facial approximation system for approximating a soft tissue profile of a skull of an unknown subject. The facial approximation system can comprise a database comprising a plurality of known skeletal datasets, wherein each skeletal dataset is associated with a known subject and is indicative of a plurality of selected cephalometric characteristics of a skull of the known subject. The facial approximation system can further comprise a processor in operative communication with the database. The processor can be configured to receive an unknown skeletal dataset comprising a plurality of selected cephalometric characteristics of the skull of the unknown subject. The processor can be further configured to compare the unknown skeletal dataset to the plurality of known skeletal datasets. The processor can be still further configured to determine the known skeletal dataset of the plurality of known skeletal datasets that most closely matches the unknown skeletal dataset, wherein the known skeletal dataset that most closely matches the unknown skeletal dataset approximates the skeletal soft tissue profile of the unknown subject.

In a further aspect, disclosed herein is a facial approximation method for approximating a soft tissue profile of a skull of an unknown subject. The facial approximation method can comprise measuring a plurality of selected cephalometric characteristics of the skull of the unknown subject. The facial approximation method can further comprise accessing a database comprising a plurality of skeletal datasets, wherein each skeletal dataset of the plurality of skeletal datasets is associated with a known subject and is indicative of a plurality of selected cephalometric characteristics of a skull of the known subject. The facial approximation method can still further comprise comparing, through a processor in operative communication with the database, the plurality of selected cephalometric characteristics of the skull of the unknown subject to the plurality of skeletal datasets. The facial approximation method can still further comprise determining, through the processor, the skeletal dataset of the plurality of skeletal datasets that most closely matches the soft tissue profile of the unknown subject.

Additional advantages of the disclosed system and method will be set forth in part in the description which follows, and in part will be understood from the description, or may be learned by practice of the disclosed system and method. The advantages of the disclosed system and method will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed system and method and together with the description, serve to explain the principles of the disclosed system and method.

FIG. 6 is a table showing exemplary weights that can be assessed to particular measurements of the skull, as further disclosed herein.

FIG. 7 is a table that describes the three faces associated with the datasets that most closely matched an unknown skull following application of a comparison algorithm, as well as three random faces, which together form a pool of six faces.

FIG. 9 shows the expert face pool assessment rankings for a first face pool.

FIG. 10 shows the expert face pool assessment rankings for a second face pool.

FIG. 11 shows the expert face pool assessment rankings for a third face pool.

FIG. 14 is a flowchart depicting an exemplary facial approximation method as disclosed herein.

FIG. 16 depicts an exemplary lateral cephalogram and analysis of a random child during an experiment as disclosed herein.

DETAILED DESCRIPTION

Figure 1:
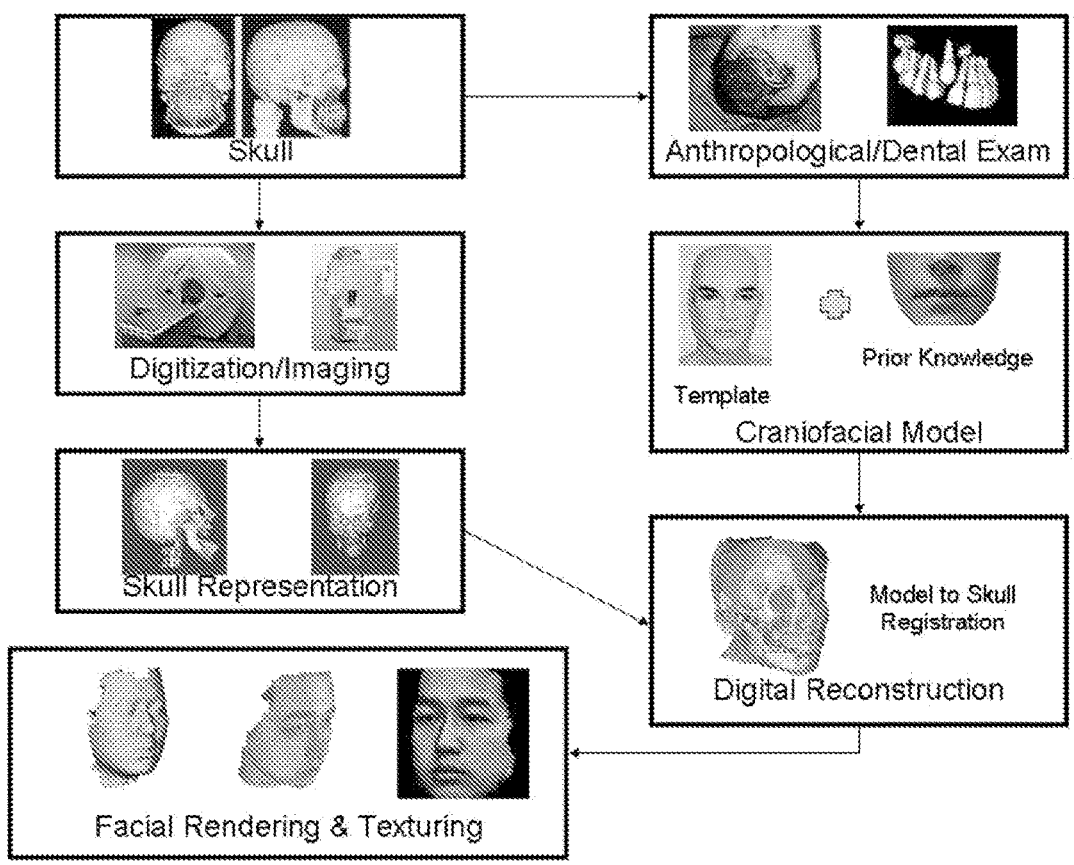
FIG. 1 schematically depicts prior art approaches to facial approximation.

The disclosed system and method may be understood more readily by reference to the following detailed description of particular embodiments and the examples included therein and to the Figures and their previous and following description.

A. Definitions

It is to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural references unless the context clearly dictates otherwise. Thus, for example, reference to "a database" includes a plurality of such databases, and reference to "the database" is a reference to one or more databases and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range¬ from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Facial Approximation Systems and Methods

Figure 2:
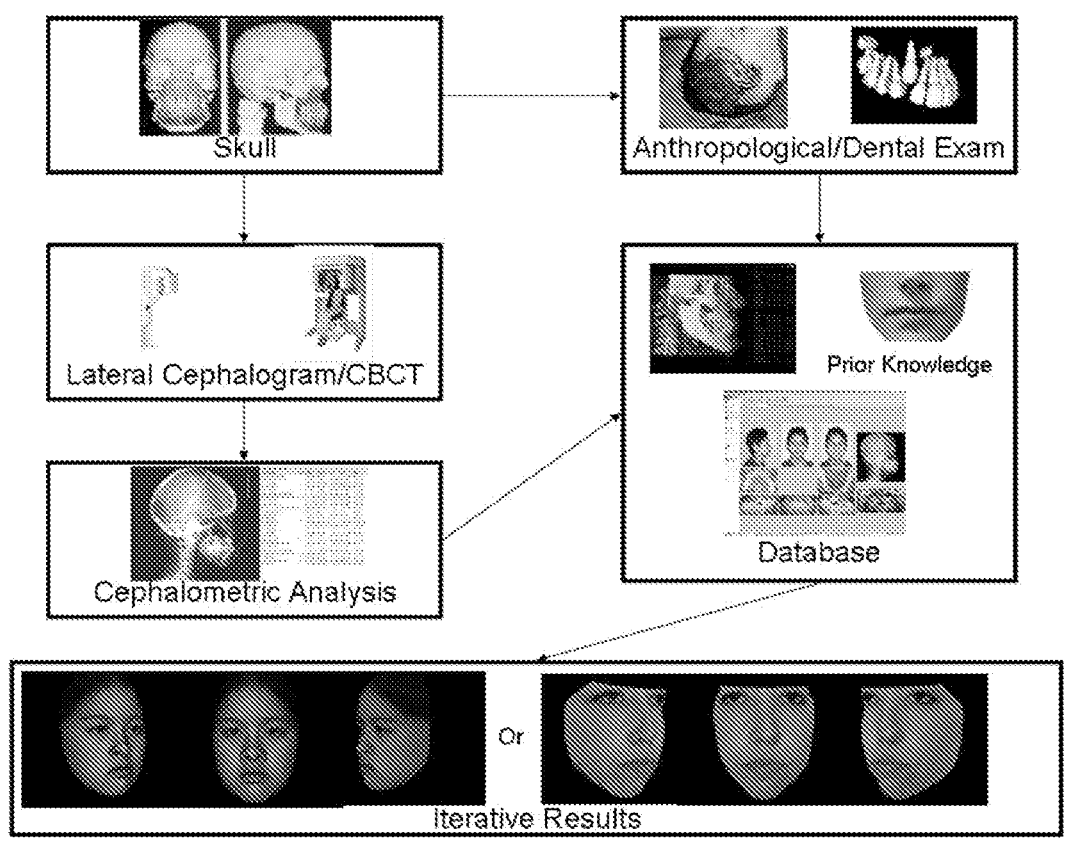
FIG. 2 is a schematic diagram depicting an exemplary facial approximation system method as disclosed herein.

Disclosed herein with reference to FIGS. 2-18 are systems and methods for approximating a soft tissue profile of a skull of an unknown subject, such as, for example and without limitation, a missing person. As further described herein, the disclosed systems and methods can utilize lateral cephalometric analysis and a comprehensive orthodontic database to determine at least one of the sex, the ethnicity, or a soft tissue profile of the unknown subject. It is contemplated that the landmarks and measurements from the lateral cephalogram are relatively unique variables that can be used as a "fingerprint" pattern of the skull of the known subject and matched closely to another individual in a large database. It is further contemplated that lateral cephalograms and their analyses exist for almost every individual who has undergone orthodontic treatment, potentially allowing for radiographs and photographs from millions of individuals to be available in a comprehensive database. Once a match is found, facial photographs, radiographs and other orthodontic records of the match can be retrieved from the database. It is further contemplated that individuals with similar lateral cephalograms and skeletal structure will have similar facial appearances. In addition to the conventional orthodontic records of dental study models, extra-oral and intra-oral photographs, and panoramic and lateral cephalograms, a cone-beam CT scan can be performed, and the height, weight (body mass index), and neck girth of individuals can be recorded. It is contemplated that these variables can be utilized to further refine database queries. It is contemplated that the systems and methods disclosed herein can provide improved approximations of facial soft tissue profiles compared to conventional digital techniques, which typically implement a generic skull template, digitize the skull surfaces, deform the craniofacial template, and register the model to the skull (FIG. 1). In contrast, the disclosed systems and methods eliminate many of these steps and their associated potential for error and subjectivity by utilizing data from individuals (FIG. 2). Thus, it is contemplated that the disclosed systems and methods can be more efficient than conventional methods because a model does not have to be estimated and constructed, and the search result can be validated against the database since the known individual has photographs and other records available. Further, it is contemplated that the disclosed systems and methods can rapidly produce a representation of a skeletally similar facial approximation, making it possible to produce multiple iterations at very little cost and in a matter of minutes. In contrast, current manual methods require approximately two weeks or more to produce a result. It is contemplated that the efficiency and automation of the disclosed systems and methods can have particular utility in mass identification efforts, whereas current methods are not particularly scalable.

Figure 3:
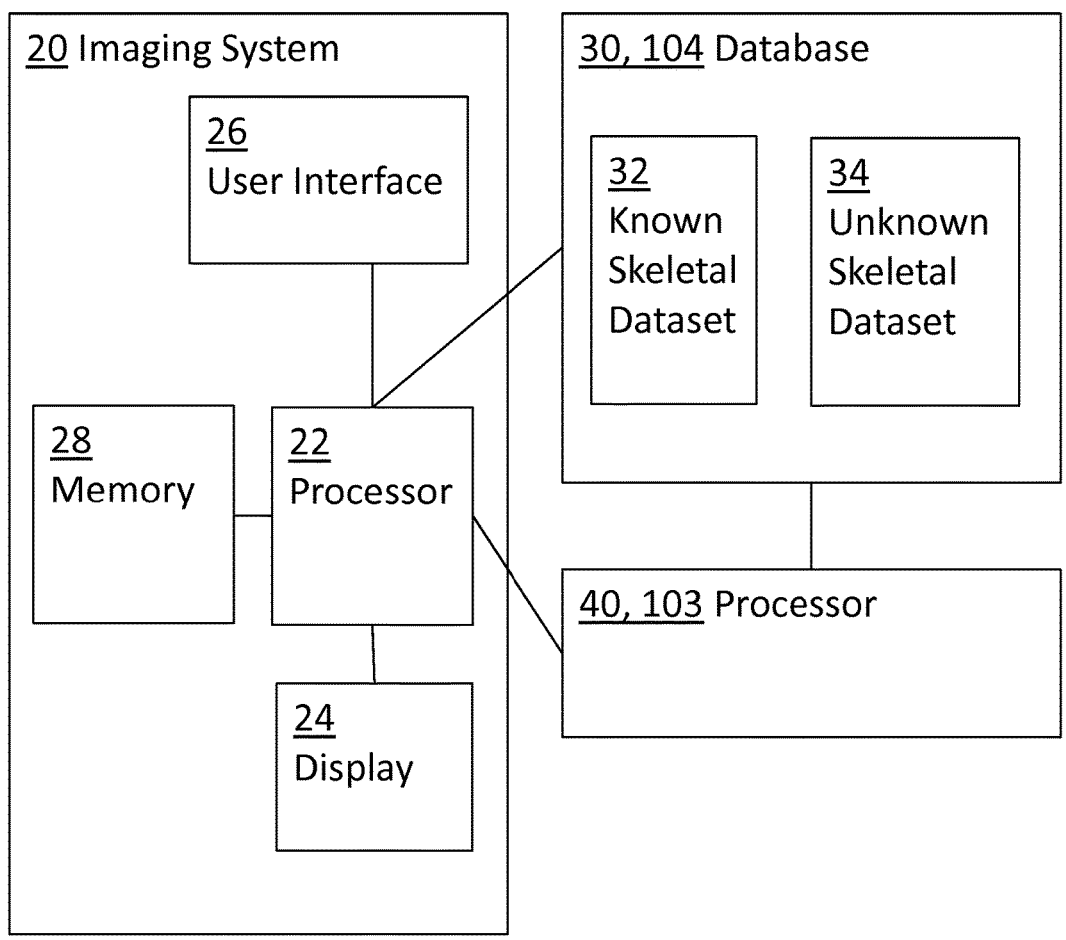
FIG. 3 is a schematic diagram depicting an exemplary facial approximation system as disclosed herein.
Figure 4:
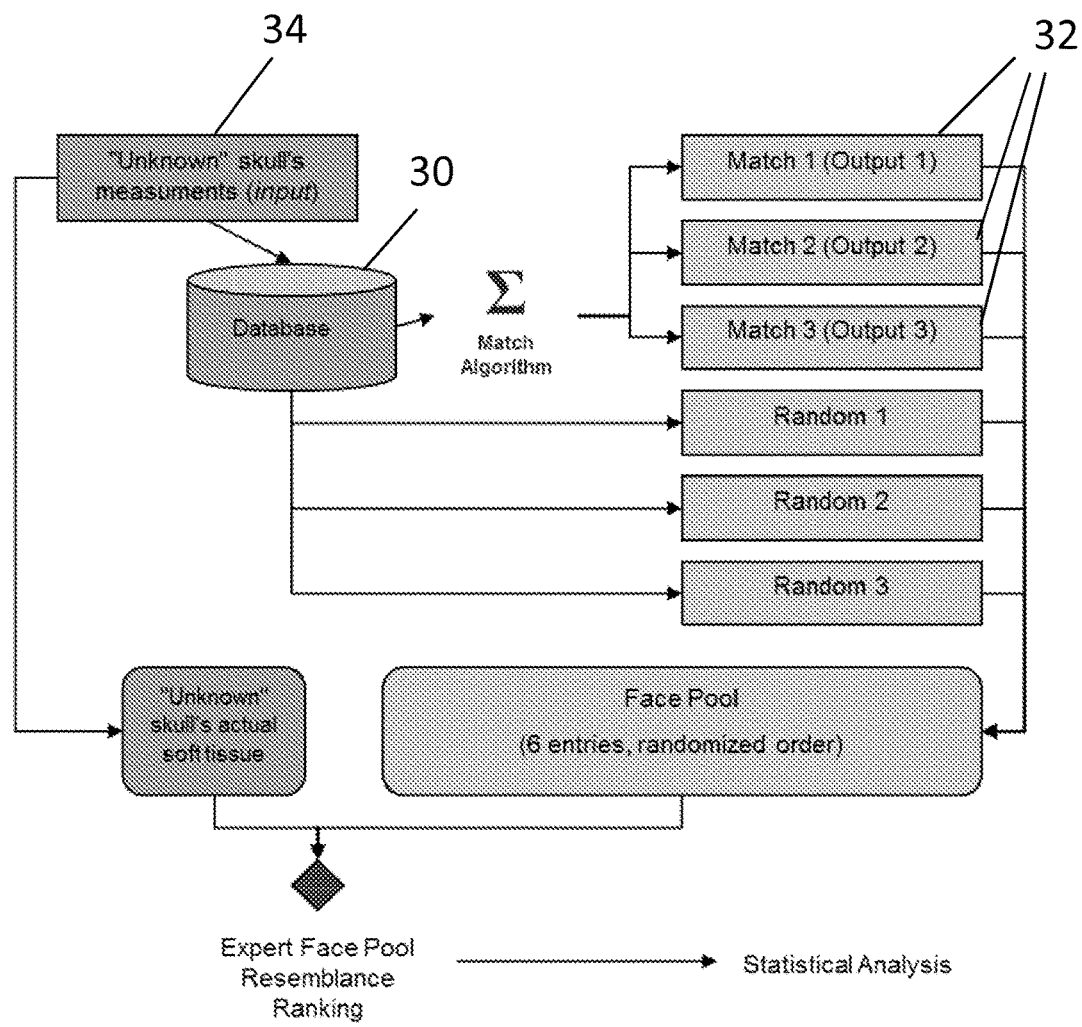
FIG. 4 is a schematic diagram depicting an exemplary facial approximation method as disclosed herein.
Figure 5:
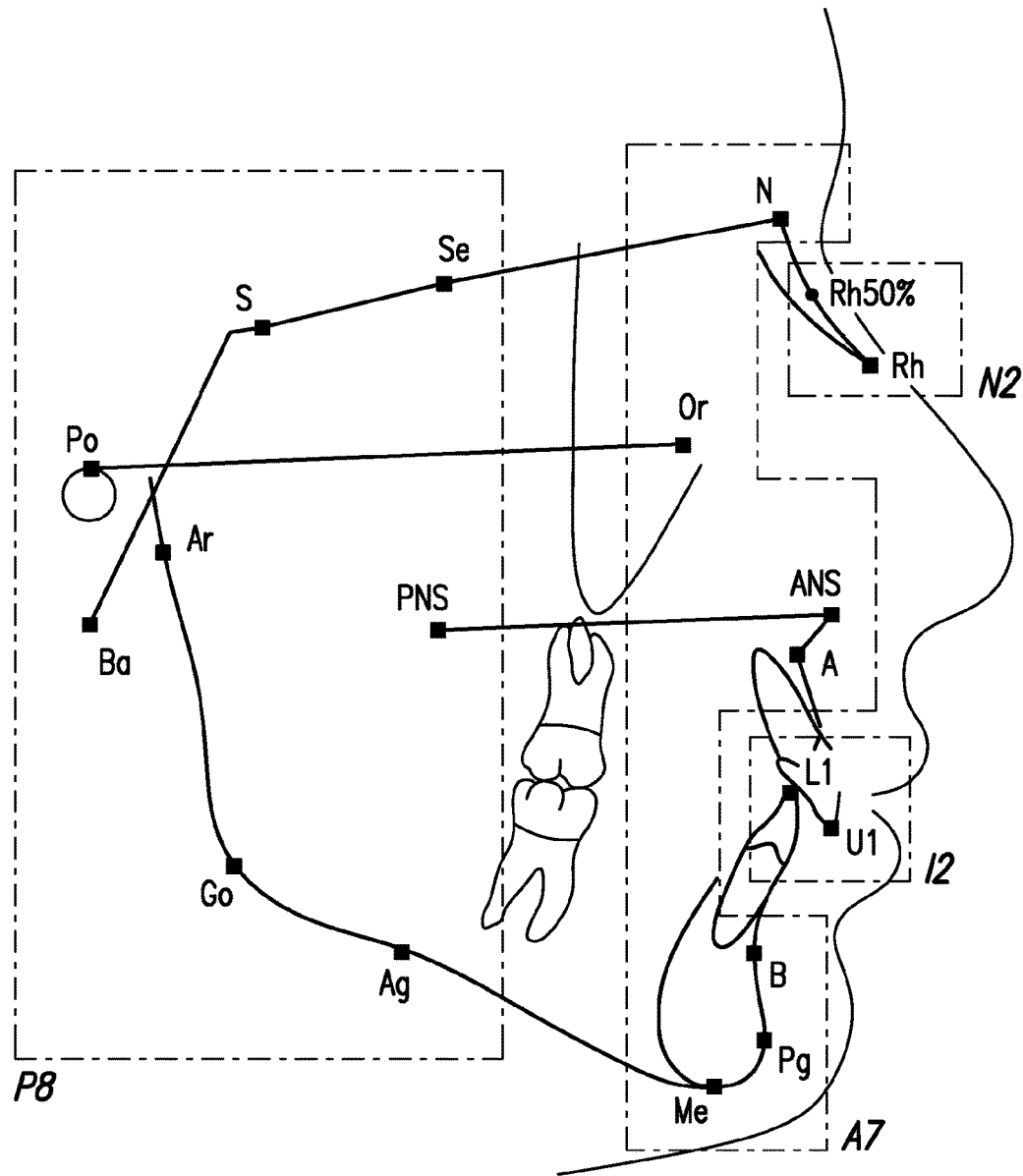
FIG. 5 is a facial diagram showing exemplary skull measurement points, as further disclosed herein.

In one exemplary aspect, and with reference to FIGS. 3-4, a facial approximation system 10 for approximating a soft tissue profile of a skull of an unknown subject can comprise a database 30 and a processor 40 positioned in operative communication with the database. In another aspect, the database 30 can comprise a plurality of known skeletal datasets 32. It is contemplated that each skeletal dataset 32 can be associated with a known subject and be indicative of a plurality of selected cephalometric characteristics of a skull of the known subject. As used herein, the term "plurality of selected cephalometric characteristics" can correspond to known cephalometric landmarks or variables. In exemplary aspects, at least one of the selected characteristics of the plurality of selected cephalometric characteristics can be selected from the group consisting of the following landmarks: N, A Point, Ba, Po, Pt, B Point, Pg, PM, UIE, LIE. Exemplary, non-limiting landmarks are schematically depicted in FIG. 5. In other exemplary aspects, it is contemplated that at least one of the selected characteristics of the plurality of selected cephalometric characteristics can correspond to an angular cephalometric variable, such as, for example and without limitation, the GMSN angle between the glabella to metopion line and the sella to nasion line, the GMFH angle between the glabella to metopion line and the porion to orbitale line, the GMBaN angle between the glabella to metopion line and the basion to nasion line, the GSgM angle between the metopion to supraglabellare line and the supraglabellare to glabella line, the IOpSN angle between inion to opisthocranion line and the SN line, the IOpFH angle between inion to opisthocranion line and the FH line, the IOpBaN angle between the inion to opisthocranion line and the BaN line, and the OIOp angle between the opisthrocranion to inion line and the inion to opisthion line. In other exemplary aspects, it is contemplated that at least one of the selected characteristics of the plurality of selected cephalometric characteristics can correspond to a linear cephalometric variable, such as, for example and without limitation, the SgGM distance between supraglabellare and the glabella to metopion line, the GSgN distance between glabella and the supraglabellare to nasion line, the FSHt frontal sinus height, vertical parameters of the frontal sinus cavity, the FsWd frontal sinus width on bregma to nasion line, the IOpO distance between inion and opisthocranion to opisthion line, the MaSN distance between mastoidale and the SN line, the MaFH distance between mastoidale and the FH line, the MaHt mastoid height from cranial base, the MaWd mastoid width at the level of cranial base, the UL thickness distance between UL to UIF, the LAFH distance between ANS to Me line, the Pfh distance from ramus height in mm from Ar tangent to ascending ramus to Mandibular plane(Go to Me), the AfhPfh palatal plane(ANS-PNS) to Me in relation to Pfh, and the Tc distance from bony Pogonion to soft tissue Pogonion. In still other exemplary aspects, it is contemplated that at least one of the selected characteristics of the plurality of selected cephalometric characteristics can correspond to a proportional-percentage cephalometric variable, such as the GPI glabella projection index, which corresponds to the distance between glabella and the supraglabellare to nasion X 100/distance between supraglabellare and nasion. In further exemplary aspects, it is contemplated that at least one of the selected characteristics of the plurality of selected cephalometric characteristics can correspond to a cephalometric ratio, such as, for example and without limitation, the ULTc ratio of total chin thickness to upper lip thickness (usually 1:1) and the AfhPfh palatal plane(ANS-PNS) to Me in relation to Pfh ratio (usually ranging between 0.65-0.75).

In exemplary aspects, it is contemplated that at least one of the selected characteristics of the plurality of selected cephalometric characteristics can correspond to a landmark or variable recognized by the American Board of Orthodontics (ABO) as part of a clinical examination, such as, for example and without limitation, the landmarks and variables disclosed in Cangialosi T J, et al., "The ABO discrepancy index: a measure of case complexity," Am J Orthod Dentofacial Orthop. 2004 March; 125 (3): 270-8, which is hereby incorporated herein by reference in its entirety. However, it is contemplated that each selected characteristic of the plurality of selected cephalometric characteristics can correspond to cephalometric landmarks or variables disclosed in Leonardi R, et al., "An evaluation of cellular neural networks for the automatic identification of cephalometric landmarks on digital images," J Biomed Biotechnol. 2009; 2009:717102; Sommer T, et al., "Precision of cephalometric analysis via fully and semiautomatic evaluation of digital lateral cephalographs," Dentomaxillofac Radiol. 2009 September; 38(6): 401-6; El-Fegh I, et al., "Automated 2-D cephalometric analysis of X-ray by image registration approach based on least square approximator," Cof Proc IEEE Eng Med Biol Soc. 2008; 2008:3949-52; Rueda S, et al., "An approach for the automatic cephalometric landmark detection using mathematical morphology and active appearance models," Med Image Comput Comput Assist Interv. 2006; 9(Pt 1): 159-66; and Stamm T, et al., "Computer-aided automated landmarking of cephalograms," J Orofac Orthop. 1998; 59(2): 73-81, each of which is incorporated herein by reference in its entirety.

In an additional aspect, the processor 40 of the facial approximation system 10 can be configured to receive an unknown skeletal dataset 34 comprising a plurality of selected cephalometric characteristics of the skull of the unknown subject. In a further aspect, the processor 40 of the facial approximation system can be configured to compare the unknown skeletal dataset 34 to the plurality of known skeletal datasets 32. In still a further aspect, the processor 40 of the facial approximation system 10 can be configured to determine the known skeletal dataset of the plurality of known skeletal datasets 32 that most closely matches the unknown skeletal dataset 32, wherein the known skeletal dataset that most closely matches the unknown skeletal dataset approximates the skeletal soft tissue profile of the unknown subject. In this aspect, it is contemplated that the processor 40 can be configured to determine the known skeletal dataset of the plurality of known skeletal datasets 32 that most closely matches the unknown skeletal dataset 34 by performing any suitable analysis technique, including, for example and without limitation, a Non-linear Least-Squares test, a Principle Component Analysis, or an Iteratively Re-weighted Least Squares test, on the plurality of known skeletal datasets with reference to the unknown skeletal dataset.

In another exemplary aspect, the facial approximation system 10 for approximating a soft tissue profile of a skull of an unknown subject can comprise means for measuring a plurality of selected cephalometric characteristics of the skull of the unknown subject. As further disclosed herein, the facial approximation system can further comprise a database 30 and a processor 40. In one aspect, the processor 40 can be positioned in operative communication with the database 30 and the means for measuring the plurality of selected cephalometric characteristics of the skull of the unknown subject. In another aspect, the database can comprise a plurality of skeletal datasets 32. In this aspect, each skeletal dataset can be associated with a known subject and be indicative of a plurality of selected cephalometric characteristics of a skull of the known subject. In a further aspect, the processor 40 can be configured to compare the plurality of selected cephalometric characteristics of the skull of the unknown subject to the plurality of skeletal datasets 32. In this aspect, it is contemplated that the processor 40 can be further configured to determine the skeletal dataset of the plurality of skeletal datasets 32 that most closely matches the soft tissue profile of the unknown subject. In this aspect, it is contemplated that the processor 40 can be configured to determine the skeletal dataset of the plurality of skeletal datasets 32 that most closely matches the soft tissue profile of the unknown subject by performing any suitable analysis technique, including, for example and without limitation, a Non-linear Least-Squares test, a Principle Component Analysis, or an Iteratively Re-weighted Least Squares test, on the plurality of skeletal datasets with reference to the plurality of selected cephalometric characteristics of the skull of the unknown subject.

In exemplary aspects, and with reference to FIG. 3, the means for measuring the plurality of selected cephalometric characteristics of the skull of the unknown subject can comprise an imaging system 20. In one optional aspect, it is contemplated that the imaging system 20 can comprise a lateral cephalostat. In another optional aspect, it is contemplated that the imaging system 20 can comprise a cone-beam computed tomography (CT) system. In another optional aspect, it is contemplated that the imaging system 20 can comprise a spiral CT system. In a further optional aspect, it is contemplated that the imaging system 20 can comprise a magnetic resonance imaging (MRI) system. In still a further optional aspect, it is contemplated that the imaging system 20 can comprise an ultrasound system. In still a further optional aspect, it is contemplated that the imaging system 20 can comprise a camera.

In one exemplary aspect, and with reference to FIG. 3, the processor 40 of the facial approximation system can be a first processor, and the imaging system 20 can comprise a second processor 22 configured to measure the plurality of selected cephalometric characteristics based upon a plurality of inputs received from a user. In this aspect, it is contemplated that each input of the plurality of inputs can be indicative of a respective cephalometric dimension or variable marked on an image of the skull of the unknown subject. It is further contemplated that the second processor 22 can be configured to determine the value of each respective cephalometric dimension or variable. In an additional aspect, the imaging system 20 can further comprise a display 24 configured to display the image of the skull of the unknown subject. In this aspect, the imaging system 20 can further comprise a user interface 26 configured to receive the plurality of inputs from the user. In a further aspect, the second processor 22 can be configured to produce on the display 24 a visual depiction of the dimension or variable associated with each respective input of the plurality of inputs. In this aspect, it is contemplated that user interface 26 can comprise, for example and without limitation, at least one of a keyboard, a keypad, a mouse, or a joystick configured to permit a user to mark the location of selected dimensions or variables on an image of the skull of the unknown subject. In further exemplary aspects, the imaging system 20 can comprise a memory 28 that is positioned in operative communication with the processor 22 of the imaging system. In these aspects, it is contemplated that the memory 28 can store software required for operation of the imaging system 20, as well as images and other data produced by the imaging system and received by the processor 22. In additional aspects, it is contemplated that the processor 40 of the facial approximation system 10 can be configured to instruct the processor 22 of the imaging system to transmit datasets or other information from the memory 28 to the processor 40 and/or to the database 30.

In exemplary aspects, it is contemplated that the facial approximation system 10 can further comprise a display 45 that is positioned in operative communication with the processor 40. In these aspects, and as further disclosed herein, it is contemplated that the processor 40 can be configured to convert one or more skeletal datasets 32, 34 from the database 30 to images 50 that can be displayed on the display 45. It is contemplated that the display 45 can be any conventional display as is known in the art.

In still further exemplary aspects, it is contemplated that the functions of the processors 22 and 40 can be combined into a single processing unit that is positioned in communication with the imaging system 20 and the database 30.

In operation, and with reference to FIGS. 4 and 13-16, the disclosed facial approximation system 10 can be used in a facial approximation method for approximating a soft tissue profile of a skull of an unknown subject. In one aspect, the facial approximation method can comprise measuring a plurality of selected cephalometric characteristics of the skull of the unknown subject. In another aspect, the facial approximation method can comprise accessing a database comprising a plurality of skeletal datasets. In this aspect, it is contemplated that each skeletal dataset of the plurality of skeletal datasets can be associated with a known subject and be indicative of a plurality of selected cephalometric characteristics of a skull of the known subject. In an additional aspect, the facial approximation method can comprise comparing, through a processor in operative communication with the database, the plurality of selected cephalometric characteristics of the skull of the unknown subject to the plurality of skeletal datasets. In a further aspect, the facial approximation method can comprise determining, through the processor, the skeletal dataset of the plurality of skeletal datasets that most closely matches the soft tissue profile of the unknown subject.

In one exemplary aspect, the facial approximation method can further comprise displaying an image corresponding to the skeletal dataset of the plurality of skeletal datasets that most closely matches the soft tissue profile of the unknown subject.

In another exemplary aspect, it is contemplated that the step of determining, through the processor, the skeletal dataset of the plurality of skeletal datasets that most closely matches the soft tissue profile of the unknown subject, can comprise performing at least one of a Non-linear Least-Squares test, a Principle Component Analysis, or an Iteratively Re-weighted Least Squares test on the plurality of skeletal datasets with reference to the plurality of selected cephalometric characteristics of the skull of the unknown subject.

In an additional exemplary aspect, it is contemplated that the plurality of selected cephalometric characteristics of the skull of the unknown subject can be measured within a common plane. For example, in this aspect, it is contemplated that each selected cephalometric characteristic of the plurality of selected cephalometric characteristics can be measured with reference to a two-dimensional image of the skull of the unknown subject.

In a further exemplary aspect, it is contemplated that at least one selected cephalometric characteristic of the plurality of selected cephalometric characteristics of the skull of the unknown subject can be measured in a different plane than at least one other selected cephalometric characteristic of the plurality of selected cephalometric characteristics of the skull of the unknown subject. For example, in this aspect, it is contemplated that at least one selected cephalometric characteristic can be measured with reference to three-dimensional images of the skull of the unknown subject.

It is contemplated that much of what is known regarding craniofacial growth and development was garnered from research studies utilizing lateral cephalometric analysis. These studies have established which structures of the craniofacial complex are developed early on and cease further growth and which structures continue to grow for some time. For example, the growth of the cranial base generally slows by age 10-12 and essentially ceases growth by age 12-15 years of age, while the maxilla continues to grow for another 1-2 years and the mandible another 2-4 years later. Sexual dimorphism exists with certain anatomic structures such as the frontal sinus and supraorbital ridges, mandible and chin, mastoid process of the temporal bone, and overall skull dimensions. Thus, it is contemplated that the systems and methods disclosed herein can be configured to eliminate or put less priority on cephalometric landmarks associated with these structures, thereby providing more accurate results and predictions. It is further contemplated that the disclosed systems and methods can permit evaluation of an unknown skull with partial landmarks. For example, if a skull is missing the mandible as is often the case, it is contemplated that an analysis can be conducted using only the landmarks associated with the cranial base and the maxilla.

It is contemplated that the database can comprise information (e.g., selected cephalometric characteristics) on any number of known individuals. In exemplary aspects, it is contemplated that the database can comprise patient records from over 3,500 patients, with around 35% of the patients comprising adults and around 65% of the patients comprising children and adolescents. It is contemplated that such a database can continuously grow (for example, at the rate of at least 300-400 patients per year) based on the number of patents that have had or are undergoing orthodontic treatment at a major university. It is contemplated that the wealth of data contained in the database can be used to further forensic investigations. In exemplary aspects, for each respective patient, the database can comprise at least one of the following: intra- and extra-oral photographs (frontal, ¾ view, profile); panoramic, lateral cephalometric, and CBCT 3-D scans; clinical data, including height, weight, neck girth, body mass index; sex, chronological age, ethnicity; and digital 3-D study models of the dentition. It is contemplated that the 3-D study models can be of particular value in related studies on occlusion and dental bite-mark analysis. It is further contemplated that many of the patients have had serial records (either interim or post-treatment records) over the course of many years, allowing for the possibility of conducting studies and predictions of age progression over time.

As can be appreciated, disclosed herein are data structures used in, generated by, or generated from, the disclosed method. Data structures generally are any form of data, information, and/or objects collected, organized, stored, and/or embodied in a composition or medium. A dataset stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

As will be appreciated by one skilled in the art, the disclosed system and method may take the form of an entirely hardware embodiment, an entirely software embodiment, or an embodiment combining software and hardware aspects. Furthermore, the system and method may take the form of a computer program product on a computer-readable storage medium having computer-readable program instructions (e.g., computer software) embodied in the storage medium. More particularly, the present system and method may take the form of web-implemented computer software. Any suitable computer-readable storage medium may be utilized including hard disks, CD-ROMs, optical storage devices, or magnetic storage devices.

Embodiments of the system and method are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 18:
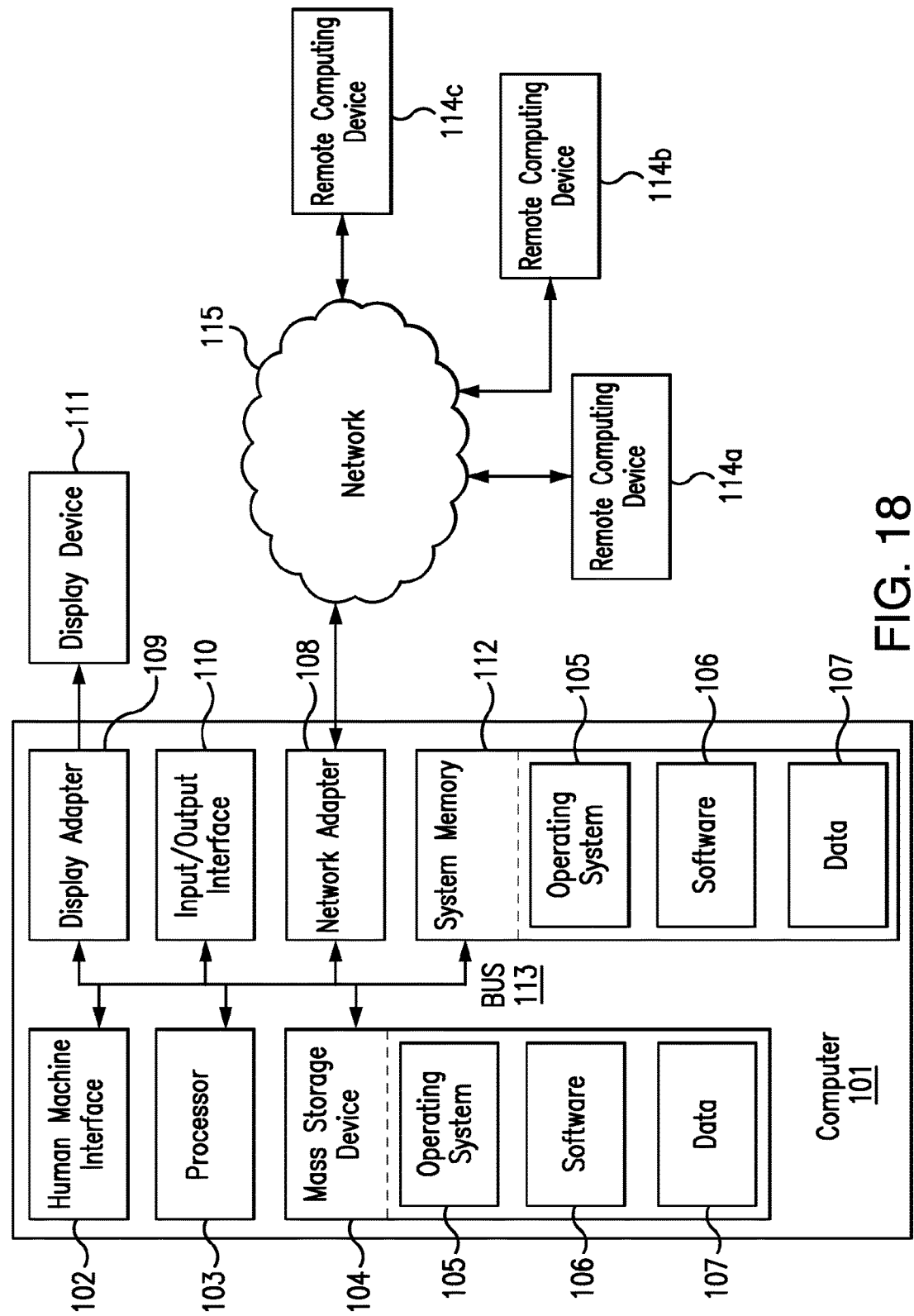
FIG. 18 is a schematic diagram of an exemplary operating environment for a computing assembly, which can include a processor as disclosed herein.

One skilled in the art will appreciate that provided herein is a functional description and that the respective functions can be performed by software, hardware, or a combination of software and hardware. In an exemplary aspect, the methods and systems can be implemented, at least in part, on a computer 101 as illustrated in FIG. 18 and described below. By way of example, the database and/or processor described herein can be part of a computer as illustrated in FIG. 18. Similarly, the methods and systems disclosed can utilize one or more computers to perform one or more functions in one or more locations. More particularly, in exemplary aspects, the database 30 and the processor 40 can be provided as part of a computer 101 as further disclosed herein. For example, with reference to FIG. 18, it is contemplated that the database 30 can be provided as part of a mass storage device 104 and that the processor 40 can be provided as a processor 103 within the computer 101. In additional exemplary aspects, it is contemplated that the display 45 can be provided as a display device 111 that is positioned in operative communication with the computer 101. In further exemplary aspects, it is contemplated that the processor 22, display 24, user interface 26, and memory 28 of the imaging system 20 can be provided as part of a computer 101 or in association with such a computer, in the same general manner as the processor 103, display device 111, human machine interface 102, and mass storage device 104 depicted in FIG. 18.

FIG. 18 is a block diagram illustrating an exemplary operating environment for performing at least a portion of the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 101. The components of the computer 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 113, and all buses specified in this description can also be implemented over a wired or wireless network connection and each of the subsystems, including the processor 103, a mass storage device 104, an operating system 105, control processing software 106, control processing data 107, a network adapter 108, system memory 112, an Input/Output Interface 110, a display adapter 109, a display device 111, and a human machine interface 102, can be contained within one or more remote computing devices 114*a,b,c* at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as control processing data 107 and/or program modules such as operating system 105 and control processing software 106 that are immediately accessible to and/or are presently operated on by the processing unit 103.

In another aspect, the computer 101 can also comprise other removable/non-removable, volatile/non-volatile computer storage media. By way of example, a mass storage device 104 can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and control processing software 106. Each of the operating system 105 and control processing software 106 (or some combination thereof) can comprise elements of the programming and the control processing software 106. Control processing data 107 can also be stored on the mass storage device 104. Control processing data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 103 via a human machine interface 102 that is coupled to the system bus 113, but can be connected by other interface and bus structures, such as a parallel port, game port, an IEEE 1394 Port (also known as a Firewire port), a serial port, a universal serial bus (USB), or) or an Intel® Thunderbolt.

In yet another aspect, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), an OLED (Organic Light Emitting Diode), or a projector. In addition to the display device 111, other output peripheral devices can comprise components such as speakers (not shown) and a printer (not shown) which can be connected to the computer 101 via Input/Output Interface 110. Any step and/or result of the methods can be output in any form to an output device. Such output can be any form of visual representation, including, but not limited to, textual, graphical, animation, audio, tactile, and the like. The display 111 and computer 101 can be part of one device, or separate devices.

The computer 101 can operate in a networked environment using logical connections to one or more remote computing devices 114a,b,c. By way of example, a remote computing device can be a personal computer, portable computer, smartphone, a server, a router, a network computer, a peer device or other common network node, and so on. In exemplary aspects, a remote computing device can be an animal instrumentation assembly and/or a rodeo flag as disclosed herein. Logical connections between the computer 101 and a remote computing device 114a,b,c can be made via a network 115, such as a local area network (LAN) and/or a general wide area network (WAN). Such network connections can be through a network adapter 108. A network adapter 108 can be implemented in both wired and wireless environments. Such networking environments are conventional and commonplace in dwellings, offices, enterprise-wide computer networks, intranets, and the Internet.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of control processing software 106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, solid state, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The above-described system components may be local to one of the devices (e.g., an imaging system) or remote (e.g. servers in a remote data center, or "the cloud"). In exemplary aspects, it is contemplated that many of the system components (e.g., the database) can be provided in a "cloud" configuration.

Exemplary Applications

A. Implications for Criminal Justice Policy and Practice in the United States

It is contemplated that the disclosed systems and methods can address a central issue in forensic facial reconstruction and anthropology in the pursuit of criminal justice. When a human skull is found, often the first questions relate to sex, age and ethnicity followed by the likely facial appearance. In operation, it is contemplated that the disclosed systems and methods can be used to determine sex, ethnicity, and, ultimately, a facial likeness of the skull. It is further contemplated that these abilities can greatly enhance the tools available for forensic investigation and can expedite investigations.

B. Cost and Efficiency

It is contemplated that the disclosed systems and methods can provide cost-effectiveness and efficiency in the process of approximating a facial profile for an unknown skull. In exemplary aspects, it is contemplated that the disclosed systems and methods can eliminate the costly and time-consuming clay modeling and virtual modeling techniques that are conventionally used. As further described herein, the disclosed systems and methods can obviate the need for modeling by matching an individual(s) in a database and rapidly producing an image of facial likeness. It is contemplated that the disclosed systems and methods can reap the benefits of records and procedures such as lateral cephalometric landmarking and analysis that may have already been completed by highly skilled individuals in the course of routine orthodontic care. From this perspective, it is contemplated that there can be significantly less manual input into this process to produce a result.

C. Interoperability and Transferability

A major limitation of both manual and computer-aided forensic facial reconstruction is the high level of complexity, specialization and cost. These barriers limit the utilization of these techniques by many under-resourced centers. In contrast, it is contemplated that the disclosed systems and methods are immediately available for other groups to utilize. The radiographic equipment to obtain a lateral cephalogram is relatively common or at least available at relatively little cost compared to other digital imaging equipment, and the capability to perform lateral cephalometric analysis is already available to many. This skillset is available at any dental school or local orthodontist and is commonly taught to students and staff. It is further contemplated that a forensic investigator can partner with a university or clinic with a large database of patients and then immediately begin producing results. In addition, it is contemplated that a digital lateral cephalometric radiograph can be sent electronically to any facility of conducting the analysis disclosed herein, thereby allowing for early analysis without having to send the actual skull for analysis (a process which itself includes legal, chain of custody, and logistical issues). In the future, it is contemplated that databases may be shared with appropriate permissions to produce better results. Many cephalometric analysis software programs utilize a searchable database that allows for output in common formats such as comma-separated values (CSV) that can be imported into readily available programs such as Microsoft Excel, Access or common statistical analysis packages.

EXAMPLES

A. Example 1

This study was directed to the generation of soft tissue approximations for unknown skulls using a match generation algorithm to find structurally similar skeletal matches within a database of known orthodontic patients. Each known orthodontic patient was subjected to a cephalometric analysis, and the resulting cephalometric data was stored within the database. FIG. 1 shows an overview of the process.

All facial approximation data was stored in a database under randomized entry names and was input into a database match algorithm as desired.

The unknown skull was subjected to the same cephalometric analysis previously conducted for the known orthodontic patients. The resulting cephalometric data was input into a weighted least-sum-of-squares (WLSS) regression algorithm. The algorithm was applied to each unknown-database entry pair (99 pairs). For example, for each database entry $\beta_x$ in the database ($x \in [1,99]$), the similarity between the unknown skull ($\alpha$) and $\beta_x$ can be defined as:

$$\sum_{i=1}^{19} \sqrt{W_i(M_{i\alpha} - M_{i\beta_x})^2},$$

where:
W=relative weight (ranges from 0 to 1);
$M_\alpha$=measurement for the unknown skull;
$M_\beta$=measurement for the known skull (database entry); and
i=number of variables considered.

Weight assignments were provided wherein the weights reflected the relative importance of each measurement (FIG. 6). The weights were assigned based on the teachings of Halazonetis et al 2007 (Morphometric correlation between facial soft-tissue profile shape and skeletal pattern in children and adolescents. American journal of orthodontics and dentofacial orthopedics, 132 (4), 450-457, 2007), which is incorporated herein by reference in its entirety. It is contemplated that the number of variables (i) can be increased for improved accuracy. It is further contemplated that the number of variables (i) can be decreased in the event a portion of the unknown skull is missing and, therefore, not measured.

To test the process, an entry was selected at random and removed from the database. The removed entry was then treated as random (leave-one-out cross-validation). Algorithm scores were calculated for all entries relative to these unknown and face pools (FIG. 7) are created.

Figure 8:
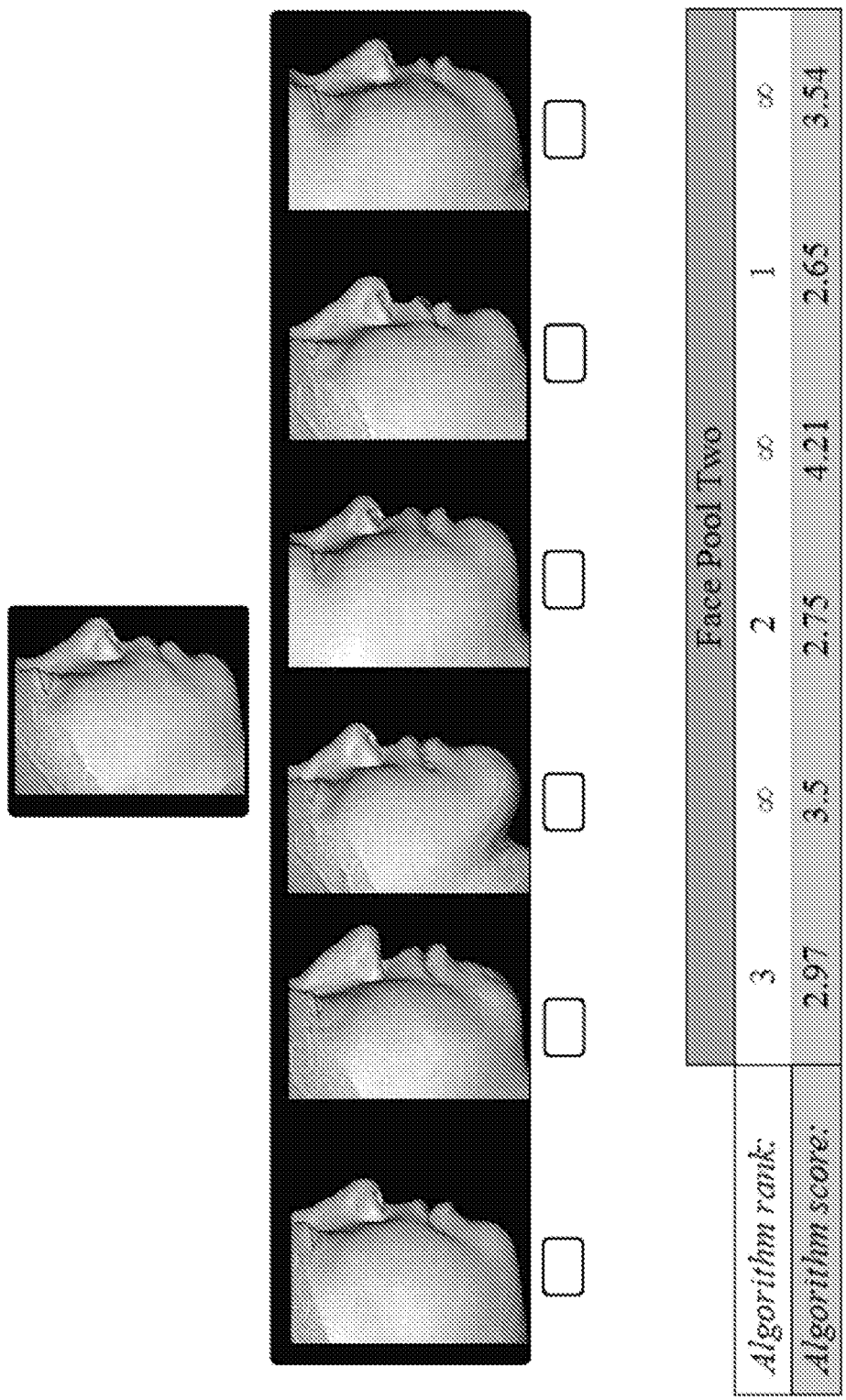
FIG. 8 provides a visual comparison of the six faces of the pool of FIG. 7 and an unknown facial profile.
Figure 12:
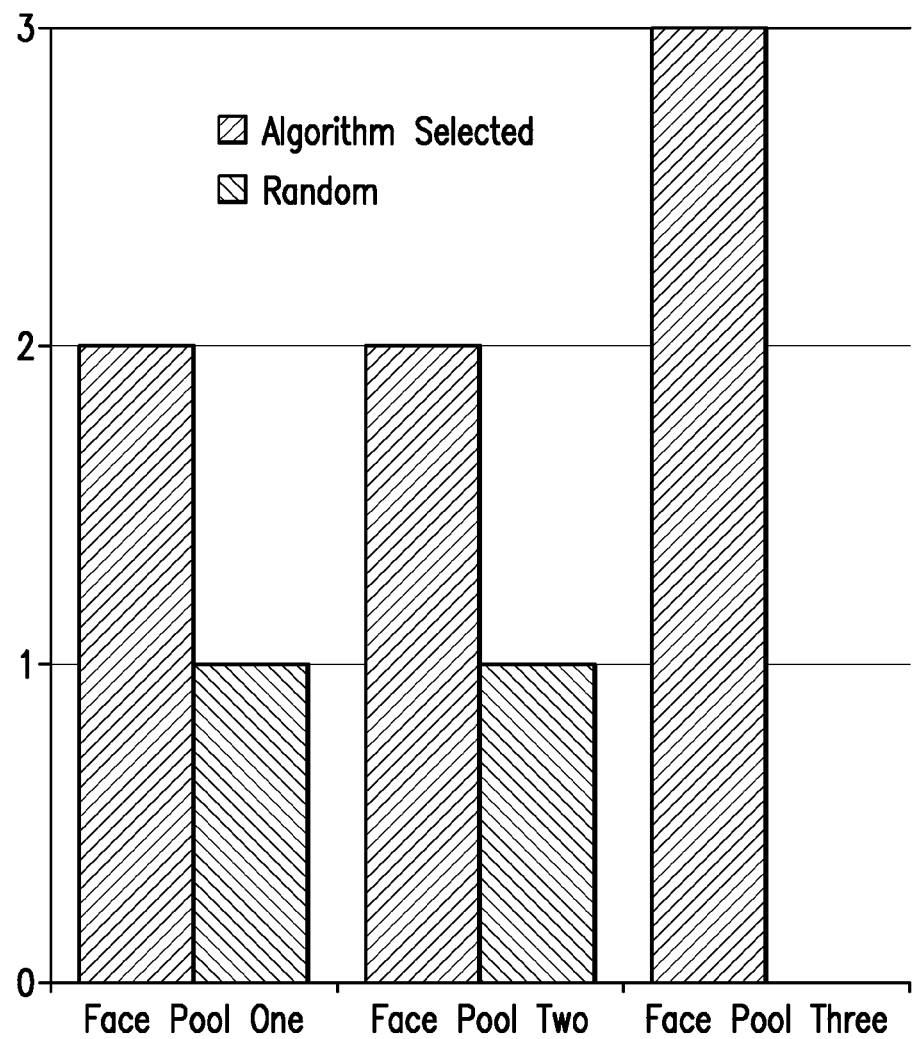
FIG. 12 is a bar graph showing the three top-ranked faces for each of the face pools described in FIGS. 9-11: algorithm versus random. For each face pool, the majority of the three top-ranked faces were identified by the algorithm.
Figure 13:
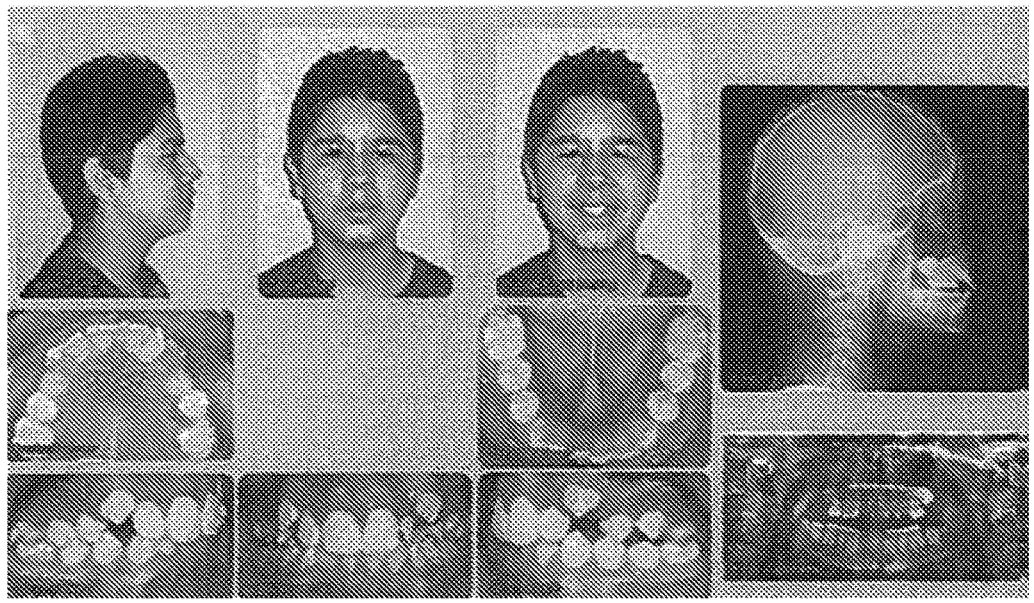
FIG. 13 depicts an exemplary skeletal dataset, including photos and x-rays from an orthodontics patient.

As shown in FIG. 7, the top three algorithm choices were combined with three random entries to form a group of 6 faces. FIG. 8 shows the faces in Face Pool Two. Expert face pool assessment rankings are provided in FIGS. 9-11. FIG. 12 confirmed that the algorithm worked better than random selection methods.

B. Example 2

Figure 15A:
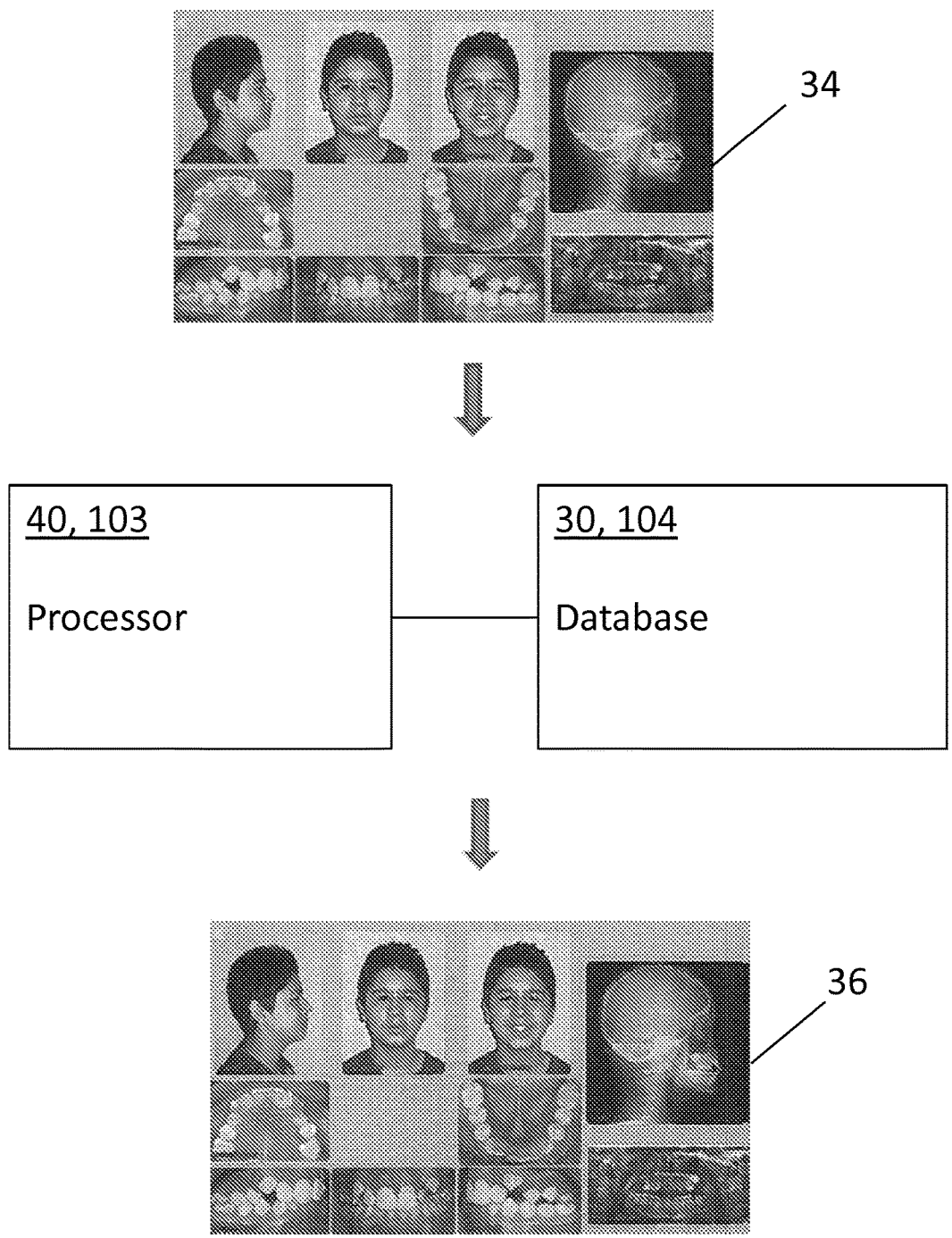
FIG. 15A schematically shows an experiment where the patient of FIG. 14 was treated as an unknown and the patient of FIG. 14 was not excluded from the database. As shown, the cephalometric analysis correctly identified the patient himself as the closest match.

A study was performed on a set of orthodontic patients. In this study, a random patient shown in FIG. 13 was chosen as the "unknown" patient. In one set of experiments, the "unknown" patient was included in the database as shown in FIG. 15A. Based on an x-ray of the patient's profile, a lateral cephalometric analysis was performed. The numbers were run through the database. The end result showed one patient as the closest match, and that patient was the profile of the "unknown" patient.

Figure 15B:
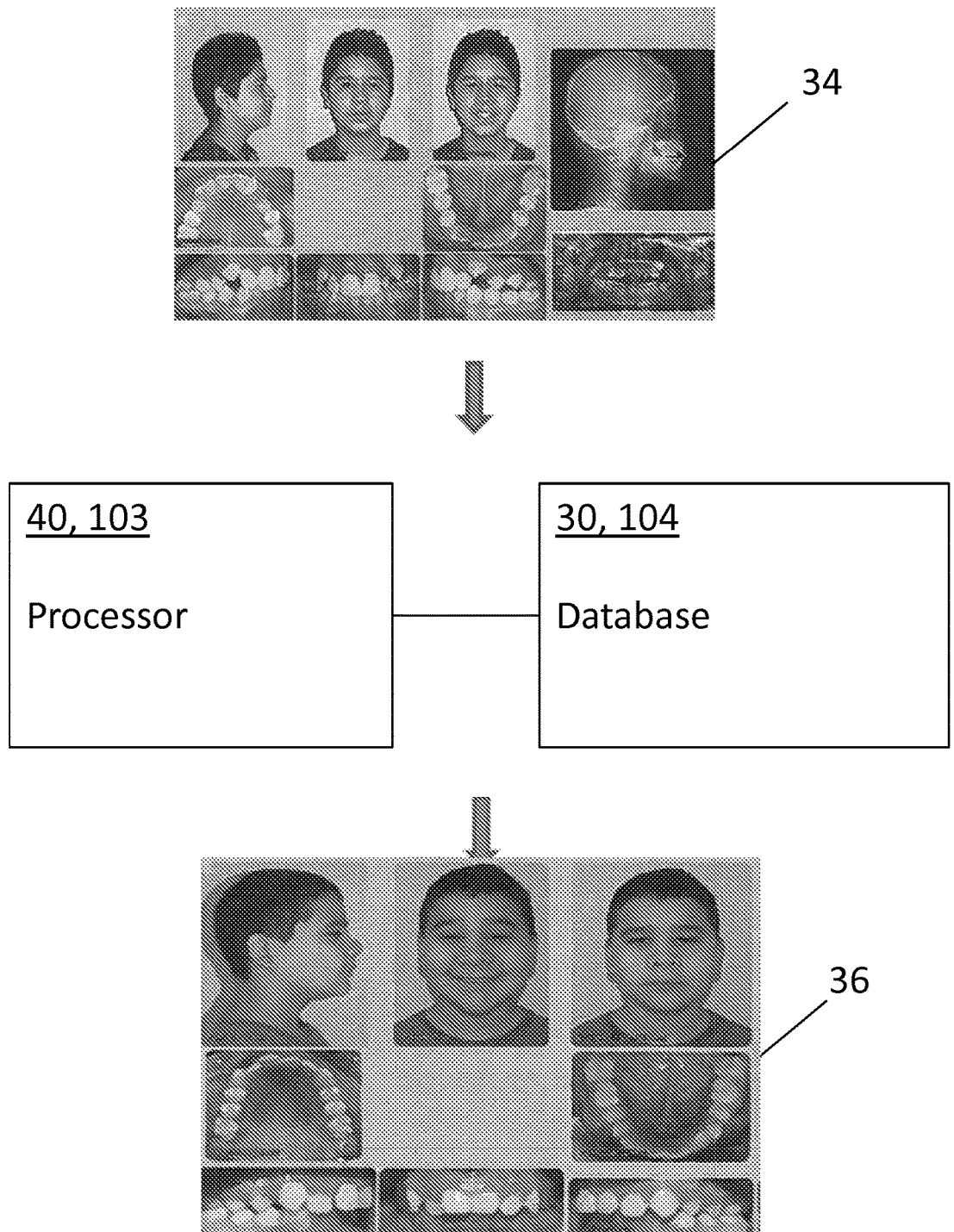
FIG. 15B schematically shows an experiment where the patient of FIG. 14 was treated as an unknown and the patient of FIG. 14 was excluded from the database. As shown, the cephalometric analysis identified the closest match to the patient.

This study was taken a step further and the "unknown" patient was not included in the database (FIG. 15B). Again, based on an x-ray of the patient's profile, a lateral cephalometric analysis was performed, and the numbers were run through the database. The end result showed one patient as the closest match. As shown in FIG. 15B, the closest match shows an individual of Hispanic descent (like the "unknown" patient) that resembles the "unknown" patient.

C. Example 3

Methods of sex determination, ethnicity determination, and facial approximation using lateral cephalometric analysis were investigated.

1. Calibration of Investigators

Lateral cephalograms were landmarked utilizing conventional cephalometric variables and analyzed using InVivo Dental 5.1 software (Anatomage, San Jose, Calif.). All investigators involved with lateral cephalometric analysis were calibrated by landmarking and tracing a set of ten selected lateral cephalometric radiographs, representing two from each of the 6-9, 9-12, 12-15, 15-18, >18 year (adult) age groups at three different sittings. Mean values, standard deviations and coefficients of variation were calculated for all variables. Intra- and inter-examiner reliability was tested using intraclass correlation coefficients (ICC), with values of 0.9 deemed as excellent and above 0.75 as good reliability. If a values less than 0.75 was found, then a review of the errors and remediation of the investigator(s) was conducted to achieve acceptable operator reliability.

2. Reliability of Lateral Cephalometric Analysis in Determination of Sex

Five groups of 6-9, 9-12, 12-15, 15-18, >18 year olds (adult) in each of the ethnic categories of Caucasians, Asians, Hispanics and African-Americans resulting in 20 groups of 50 males and 50 females (total 2000) were studied. Subjects were randomly selected from the orthodontic record database until a category was filled. Lateral cephalometric radiographs were de-identified and assigned a random number utilizing the MICROSOFT EXCEL (Microsoft, Redmond, Wash.) random number generator function. Investigators working on the cephalometric analysis were blinded. Testing was conducted on conventional cephalometric variables disclosed by Patil, K R, et al., "Determination of sex by discriminant function analysis and stature by regression analysis: a lateral cephalometric study," Forensic Science International 147 (2005) 175-180, and Hsiao, T-H, et al., "Sex determination using discriminant function analysis in children and adolescents: a lateral cephalometric study," Int J Legal Med (2010) 124:155-160, both of which are incorporated herein by reference in their entirety. Preliminary results (see below) and pre-hoc analysis showed high reliability (95%) in a sample of 20 males and 20 females, suggesting that 50 males and 50 females is an adequate sample size in each group to address the hypothesis. Reliability was expressed as the percentage of correct classifications. Mean values, standard deviations and coefficients of variation were calculated for all variables. The values were compared between both the sexes using Student's t-test.

3. Reliability of Other Lateral Cephalometric Variables in Determination of Sex

The same groups from above were analyzed using Jarabak and Rickett's cephalometric analysis, as described in Jarabak, J R, Technique and treatment with the light wire appliance. 2nd edn. St Louis: C V Mosby; 1973; and Ricketts, R M, Roth R H, Chaconas S J, Schulhof R J, Engel A. Orthodontic Diagnosis and Planning Vols. 1 and 2, Denver, Rocky Mountain Orthodontics, 1982, both of which are hereby incorporated by reference in their entirety. Variables associated with the chin, length and angle of the mandible and anterior and posterior facial heights were of particular interest. Statistical analysis of the cephalometric variables was conducted using Fisher's discriminant analysis for sex determination essentially following the method of Patil and Mody, 2004. A discriminant function was derived for variables, and a discriminant score was calculated for individuals by substituting recorded measurements into the function. Male and female groups were divided by a sectioning point at which there was minimum overlap between the two groups. Calculations of discriminant functions were performed by solving n equations, where n=number of cephalometric variables, shown in matrix notation S=DL, where L is the vector of the co-efficient of discriminant functions, S is the pooled dispersion matrix, and D is the vector of elements representing differences between the mean of the two groups. Separation between the groups will be calculated using the Mahalanobis $D^2$ statistic. The significance of $D^2$ is estimated by the F statistic.

$$F = \frac{N_1 N_2 (N_1 + N_2 - p - 1)}{p(N_1 + N_2)(N_1 + N_2 - 2)} \times D^2$$

Where $N_1$ and $N_2$ are the size of the male and female samples, respectively, and p is the number of variables.

$$D^2 = \sum_{i=1}^{n} \sum_{k=1}^{n} c_{ik} d_i d_k$$

Where $C_{ik}$ is the inverted matrix for the co-efficient and $d_i$ and $d_k$ and a matrix for the production of mean differences. Reliability will be expressed as the percentage of correct classifications.

4. Reliability of Lateral Cephalometric Analysis in Determination of Ethnicity

The same five groups from above were analyzed with variables associated with known cephalometric variables which are significant between the ethnicities, such as angular cephalometric variables (e.g., the GMSN angle between the glabella to metopion line and the sella to nasion line, the GMFH angle between the glabella to metopion line and the porion to orbitale line, the GMBaN angle between the glabella to metopion line and the basion to nasion line, the GSgM angle between the metopion to supraglabellare line and the supraglabellare to glabella line, the IOpSN angle between inion to opisthocranion line and the SN line, the IOpFH angle between inion to opisthocranion line and the FH line, the IOpBaN angle between the inion to opisthocranion line and the BaN line, and the OIOp angle between the opisthrocranion to inion line and the inion to opisthion line), linear cephalometric variables (e.g., the SgGM distance between supraglabellare and the glabella to metopion line, the GSgN distance between glabella and the supraglabellare to nasion line, the FSHt frontal sinus height, vertical parameters of the frontal sinus cavity, the FsWd frontal sinus width on bregma to nasion line, the IOpO distance between inion and opisthocranion to opisthion line, the MaSN distance between mastoidale and the SN line, the MaFH distance between mastoidale and the FH line, the MaHt mastoid height from cranial base, the MaWd mastoid width at the level of cranial base, the UL thickness distance between UL to UIF, the LAFH distance between ANS to Me line, the Pfh distance from ramus height in mm from Ar tangent to ascending ramus to Mandibular plane (Go to Me), the AfhPfh palatal plane(ANS-PNS) to Me in relation to Pfh, and the Tc distance from bony Pogonion to soft tissue Pogonion), proportional-percentage cephalometric variables (e.g., the GPI glabella projection index), and cephalometric ratios (e.g., the ULTc ratio of total chin thickness to upper lip thickness and the AfhPfh palatal plane(ANS-PNS) to Me in relation to Pfh ratio). These variables are generally associated with the anterior-posterior position of the maxilla and mandible, and the relationship of the maxillary and mandibular incisors to the skeletal base and to each other. Mean values, standard deviations and coefficients of variation were calculated for all variables. As described above, a discriminant function was derived for variables and a discriminant score was calculated for individuals by substituting recorded measurements into the function. Reliability was expressed as the percentage of correct classifications.

5. Lateral Cephalometric Analysis and Facial Approximation

Common lateral cephalometric analyses (Jarabak and Rickett's) were used as a "fingerprint" pattern to produce a facial approximation. These analyses were selected as they provide information regarding the cranial base and relationships of the teeth to the skeleton and to each other. Additionally, ethnic variation is found in the normal values of specific variables, particularly those concerned with the incisor positions related to the skeletal base and to each other. Five random individuals from each of the five groups of 6-9, 9-12, 12-15, 15-18, >18 year olds (adult) in each of the ethnic categories of Caucasians, Asians, Hispanics and African-Americans (200 facial approximations) were closest-matched to another within their respective groups. The database match was performed using a non-linear least squares algorithm which consists of n points (pairs of variables), $(x_1, y_1)$, $l=1, \ldots, n$, where $x_1$ is an independent variable and $y_1$ is a dependent variable. The model has the form $f(x, \beta)$, where the m adjustable parameters are held in the variable $\beta$. The goal was to find the parameter values for the model which "best" fits the data. The least squares method finds its optimum when the sum, $S$, of squared residuals found by $$s = \sum_{i=1}^{n} r_i^2$$

is at a minimum. A residual, r, is the difference between the actual value of the dependent variable and the value predicted by the model:

$$r_i = y_1 - f(x_1, \beta)$$

This approach can offer flexibility for future studies in that particular variables may be given priority or weighted in a weighted least sum of squares algorithm. This has implications for skulls with missing anatomy or otherwise less reliable variables.

The match was inserted into a face pool with nine other individuals from the same respective test group for assessment. The assessors were ten random lay persons shown a photograph of the known target individual and then tasked with selection of the facial approximation that most closely resembles the target. Accuracy was reported as the percentage of correct target selection compared to chance for random selection ($1/10$).

6. Preliminary Results a. Determination of Sex in a Sample of 12-15 Year Olds

Using the 18 lateral cephalometric variables described by Hsiao in a sample of Caucasian 12-15 year olds (20 male and 20 female) the sex was correctly categorized 95% of the time in both groups. This result strongly suggests that this approach may also be of value in growing individuals.

b. Lateral Cephalometric Analysis and Facial Approximation

The lateral cephalogram of a random child was analyzed (FIG. 16) to provide independent variables. The cephalometric variables were matched to 35 individuals of the same sex, ethnicity and within 2 years of age in the database using the non-linear least squares algorithm described above.

Figure 17A:
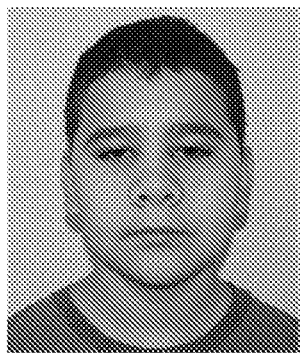
FIGS. 17A-17C provide a side-by-side comparison of the facial profiles of a random child (FIG. 17A), the closest match to the random child (FIG. 17B), and a "cartooned" version of the closest match (FIG. 17C). The closest match was determined based upon a comparison between the analysis depicted in FIG. 16 and a database containing cephalometric variables associated with 35 individuals of the same sex, ethnicity, and age group.
Figure 17B:
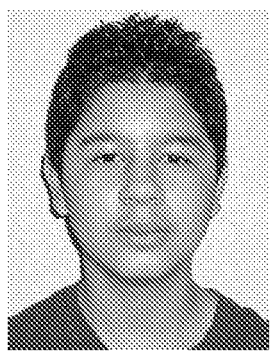
Figure 17C:
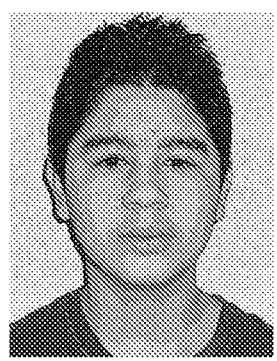

The photograph of the randomly selected child (FIG. 17A) was compared to that of the closest match (FIG. 17B). While there was some resemblance in the nose and midface, it is clear that the closest match is not identical, with different head shapes, lower facial taper, hair style and size of lips. The random child was also more heavy set than the closest match. This result showed that this approach is promising but that more development is required with a larger sample of individuals to use for matching. The results also indicated that specific individual data such as height and weight may be used to further refine the match. As shown in FIG. 17C, the photograph of the match was "cartooned" using an Adobe Photoshop filter to demonstrate that recognizable facial features can be maintained while removing individual features. The "cartooned" image is more similar to artist's drawings of faces and can serve as an alternative to use of an image of a real individual. Additionally, it is contemplated that photo editing can be used to further customize the photograph for presentation.

Exemplary Aspects

In various exemplary aspects, disclosed herein is a facial approximation system for approximating a soft tissue profile of a skull of an unknown subject, the facial approximation system comprising: an imaging system configured to measure a plurality of selected cephalometric characteristics of the skull of the unknown subject; a database comprising a plurality of skeletal datasets, each skeletal dataset being associated with a known subject and being indicative of a plurality of selected cephalometric characteristics of a skull of the known subject; and a processor in operative communication with the database and the imaging system, wherein the processor is configured to: compare the plurality of selected cephalometric characteristics of the skull of the unknown subject to the plurality of skeletal datasets; and determine the skeletal dataset of the plurality of skeletal datasets that most closely matches the soft tissue profile of the unknown subject.

In another exemplary aspect, the imaging system comprises a lateral cephalostat.

In another exemplary aspect, the imaging system comprises a cone-beam computed tomography (CT) system.

In another exemplary aspect, the imaging system comprises a spiral CT system.

In another exemplary aspect, the imaging system comprises a magnetic resonance imaging (MRI) system.

In another exemplary aspect, the imaging system comprises an ultrasound system.

In another exemplary aspect, the imaging system comprises a camera.

In another exemplary aspect, the imaging system comprises a processor configured to measure the plurality of selected cephalometric characteristics based upon a plurality of inputs received from a user. In an additional exemplary aspect, each input of the plurality of inputs is indicative of a respective cephalometric characteristic marked on an image of the skull of the unknown subject, and the processor is configured to determine the value of each respective cephalometric characteristic. In a further exemplary aspect, the imaging system comprises: a display configured to display the image of the skull of the unknown subject; and a user interface configured to receive the plurality of inputs from the user. In still another exemplary aspect, the processor of the imaging system is configured to produce on the display a visual depiction of the cephalometric characteristic associated with each respective input of the plurality of inputs.

In another exemplary aspect, the processor is configured to determine the skeletal dataset of the plurality of skeletal datasets that most closely matches the soft tissue profile of the unknown subject by performing a nonlinear least-squares test on the plurality of skeletal datasets with reference to the plurality of selected cephalometric characteristics of the skull of the unknown subject.

In another exemplary aspect, at least one cephalometric characteristic of the plurality of selected cephalometric characteristics corresponds to a cephalometric landmark.

In another exemplary aspect, at least one cephalometric characteristic of the plurality of selected cephalometric characteristics corresponds to a linear cephalometric variable.

In another exemplary aspect, at least one cephalometric characteristic of the plurality of selected cephalometric characteristics corresponds to an angular cephalometric variable.

In various exemplary aspects, disclosed herein is a facial approximation system for approximating a soft tissue profile of a skull of an unknown subject, the facial approximation system comprising: a database comprising a plurality of known skeletal datasets, each skeletal dataset being associated with a known subject and being indicative of a plurality of selected cephalometric characteristics of a skull of the known subject; and a processor in operative communication with the database, wherein the processor is configured to: receive an unknown skeletal dataset comprising a plurality of selected cephalometric characteristics of the skull of the unknown subject; compare the unknown skeletal dataset to the plurality of known skeletal datasets; and determine the known skeletal dataset of the plurality of known skeletal datasets that most closely matches the unknown skeletal dataset, wherein the known skeletal dataset that most closely matches the unknown skeletal dataset approximates the skeletal soft tissue profile of the unknown subject.

In another exemplary aspect, the processor is configured to determine the known skeletal dataset of the plurality of known skeletal datasets that most closely matches the unknown skeletal dataset by performing a nonlinear least-squares test on the plurality of known skeletal datasets with reference to the unknown skeletal dataset.

In various exemplary aspects, disclosed herein is a facial approximation method for approximating a soft tissue profile of a skull of an unknown subject, the facial approximation method comprising: measuring a plurality of selected cephalometric characteristics of the skull of the unknown subject; accessing a database comprising a plurality of skeletal datasets, each skeletal dataset of the plurality of skeletal datasets being associated with a known subject and being indicative of a plurality of selected cephalometric characteristics of a skull of the known subject; comparing, through a processor in operative communication with the database, the plurality of selected cephalometric characteristics of the skull of the unknown subject to the plurality of skeletal datasets; and determining, through the processor, the skeletal dataset of the plurality of skeletal datasets that most closely matches the soft tissue profile of the unknown subject.

In another exemplary aspect, the facial approximation method further comprises displaying an image corresponding to the skeletal dataset of the plurality of skeletal datasets that most closely matches the soft tissue profile of the unknown subject.

In another exemplary aspect, the step of determining, through the processor, the skeletal dataset of the plurality of skeletal datasets that most closely matches the soft tissue profile of the unknown subject, comprises performing a nonlinear least-squares test on the plurality of skeletal datasets with reference to the plurality of selected cephalometric characteristics of the skull of the unknown subject.

In another exemplary aspect, the plurality of selected cephalometric characteristics of the skull of the unknown subject are measured within a common plane.

In another exemplary aspect, at least one selected cephalometric characteristic of the plurality of selected cephalometric characteristics of the skull of the unknown subject is measured in a different plane than at least one other selected cephalometric characteristic of the plurality of selected cephalometric characteristics of the skull of the unknown subject.

In another exemplary aspect, at least one cephalometric characteristic of the plurality of selected cephalometric characteristics of the unknown subject corresponds to a cephalometric landmark.

In another exemplary aspect, at least one cephalometric characteristic of the plurality of selected cephalometric characteristics of the unknown subject corresponds to a linear cephalometric variable.

In another exemplary aspect, at least one cephalometric characteristic of the plurality of selected cephalometric characteristics of the unknown subject corresponds to an angular cephalometric variable.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A facial approximation system for approximating a soft tissue profile of a skull of an unknown subject, the facial approximation system comprising:
   an imaging system configured to measure a plurality of selected cephalometric characteristics of the skull of the unknown subject;
   a database comprising a plurality of skeletal datasets, each skeletal dataset being associated with a known subject and being indicative of a plurality of selected cephalometric characteristics of a skull of the known subject; and
   a processor in operative communication with the database and the imaging system, wherein the processor is configured to:
      compare the plurality of selected cephalometric characteristics of the skull of the unknown subject to the plurality of skeletal datasets; and
      determine the skeletal dataset of the plurality of skeletal datasets that most closely matches the soft tissue profile of the unknown subject by performing a nonlinear least-squares test on the plurality of skeletal datasets with reference to the plurality of selected cephalometric characteristics of the skull of the unknown subject.

2. The facial approximation system of claim 1, wherein the imaging system comprises a lateral cephalostat.

3. The facial approximation system of claim 1, wherein the imaging system comprises a cone-beam computed tomography (CT) system.

4. The facial approximation system of claim 1, wherein the imaging system comprises a spiral CT system.

5. The facial approximation system of claim 1, wherein the imaging system comprises a magnetic resonance imaging (MRI) system.

6. The facial approximation system of claim 1, wherein the imaging system comprises an ultrasound system.

7. The facial approximation system of claim 1, wherein the imaging system comprises a camera.

8. The facial approximation system of claim 1, wherein the imaging system comprises a processor configured to measure the plurality of selected cephalometric characteristics based upon a plurality of inputs received from a user.

9. The facial approximation system of claim 8, wherein each input of the plurality of inputs is indicative of a respective cephalometric characteristic marked on an image of the skull of the unknown subject, and wherein the processor is configured to determine the value of each respective cephalometric characteristic.

10. The facial approximation system of claim 9, wherein the imaging system comprises:
    a display configured to display the image of the skull of the unknown subject; and
    a user interface configured to receive the plurality of inputs from the user.

11. The facial approximation system of claim 10, wherein the processor of the imaging system is configured to produce on the display a visual depiction of the cephalometric characteristic associated with each respective input of the plurality of inputs.

12. The facial approximation system of claim 1, wherein at least one cephalometric characteristic of the plurality of selected cephalometric characteristics corresponds to a cephalometric landmark.

13. The facial approximation system of claim 1, wherein at least one cephalometric characteristic of the plurality of selected cephalometric characteristics corresponds to a linear cephalometric variable.

14. The facial approximation system of claim 1, wherein at least one cephalometric characteristic of the plurality of selected cephalometric characteristics corresponds to an angular cephalometric variable.

15. A facial approximation system for approximating a soft tissue profile of a skull of an unknown subject, the facial approximation system comprising:
- a database comprising a plurality of known skeletal datasets, each skeletal dataset being associated with a known subject and being indicative of a plurality of selected cephalometric characteristics of a skull of the known subject; and
- a processor in operative communication with the database, wherein the processor is configured to:
  - receive an unknown skeletal dataset comprising a plurality of selected cephalometric characteristics of the skull of the unknown subject;
  - compare the unknown skeletal dataset to the plurality of known skeletal datasets; and
  - determine the known skeletal dataset of the plurality of known skeletal datasets that most closely matches the unknown skeletal dataset by performing a nonlinear least-squares test on the plurality of known skeletal datasets with reference to the unknown skeletal dataset, wherein the known skeletal dataset that most closely matches the unknown skeletal dataset approximates the skeletal soft tissue profile of the unknown subject.

16. A facial approximation method for approximating a soft tissue profile of a skull of an unknown subject, the facial approximation method comprising:
- measuring a plurality of selected cephalometric characteristics of the skull of the unknown subject;
- accessing a database comprising a plurality of skeletal datasets, each skeletal dataset of the plurality of skeletal datasets being associated with a known subject and being indicative of a plurality of selected cephalometric characteristics of a skull of the known subject;
- comparing, through a processor in operative communication with the database, the plurality of selected cephalometric characteristics of the skull of the unknown subject to the plurality of skeletal datasets; and
- determining, through the processor, the skeletal dataset of the plurality of skeletal datasets that most closely matches the soft tissue profile of the unknown subject by performing a nonlinear least-squares test on the plurality of skeletal datasets with reference to the plurality of selected cephalometric characteristics of the skull of the unknown subject.

17. The facial approximation method of claim 16, further comprising displaying an image corresponding to the skeletal dataset of the plurality of skeletal datasets that most closely matches the soft tissue profile of the unknown subject.

18. The facial approximation method of claim 16, wherein the plurality of selected cephalometric characteristics of the skull of the unknown subject are measured within a common plane.

19. The facial approximation method of claim 16, wherein at least one selected cephalometric characteristic of the plurality of selected cephalometric characteristics of the skull of the unknown subject is measured in a different plane than at least one other selected cephalometric characteristic of the plurality of selected cephalometric characteristics of the skull of the unknown subject.

20. The facial approximation method of claim 16, wherein at least one cephalometric characteristic of the plurality of selected cephalometric characteristics of the unknown subject corresponds to a cephalometric landmark.

21. The facial approximation method of claim 16, wherein at least one cephalometric characteristic of the plurality of selected cephalometric characteristics of the unknown subject corresponds to a linear cephalometric variable.

22. The facial approximation method of claim 16, wherein at least one cephalometric characteristic of the plurality of selected cephalometric characteristics of the unknown subject corresponds to an angular cephalometric variable.

\* \* \* \* \*